(12) United States Patent
Kato et al.

(10) Patent No.: US 8,697,073 B2
(45) Date of Patent: Apr. 15, 2014

(54) ANTI-PODOPLANIN ANTIBODY, AND PHARMACEUTICAL COMPOSITION CONTAINING ANTI-PODOPLANIN ANTIBODY

(75) Inventors: Yukinari Kato, Yamagata (JP); Mika Kato, Yamagata (JP); Yasuhiko Nishioka, Tokushima (JP)

(73) Assignee: Fujifilm RI Pharma Co., Ltd., Tokyo (JP)

( * ) Notice: Subject to any disclaimer, the term of this patent is extended or adjusted under 35 U.S.C. 154(b) by 0 days.

(21) Appl. No.: 13/390,284

(22) PCT Filed: Sep. 30, 2010

(86) PCT No.: PCT/JP2010/067141
§ 371 (c)(1),
(2), (4) Date: Jun. 28, 2012

(87) PCT Pub. No.: WO2011/040565
PCT Pub. Date: Apr. 7, 2011

(65) Prior Publication Data
US 2012/0308571 A1 Dec. 6, 2012

(30) Foreign Application Priority Data
Sep. 30, 2009 (JP) ................................. 2009-226143

(51) Int. Cl.
*A61K 39/395* (2006.01)
(52) U.S. Cl.
USPC ................... 424/133.1; 424/138.1; 424/141.1; 424/155.1; 530/387.3; 530/387.7; 530/388.1; 530/388.8
(58) Field of Classification Search
None
See application file for complete search history.

(56) References Cited

U.S. PATENT DOCUMENTS 5,693,762 A * 12/1997 Queen et al. ................ 530/387.3

FOREIGN PATENT DOCUMENTS

WO WO 2005053742 A1 * 6/2005
WO WO 2007045477 A2 * 4/2007

OTHER PUBLICATIONS

Kato et al., Biochem Biophys Res Commun. Nov. 3, 2006;349(4):1301-7. Epub Sep. 7, 2006.*
Janeway et al., Immunobiology, 3rd edition, 1997, Garland Press, pp. 3:1-3:11.*
Rudikoff et al., Proc Natl Acad Sci USA, 1982, 79:1979-1983.*
Portolano et al., J. Immunol., 1993, 150:880-887.*
Fundamental Immunology, William E. Paul, M.D. ed., 3d ed. 1993, p. 242.*
Yukinari Kato et al.; :Prodoplanin is a novel antibody-based therapeutic target for glioblastoma; proceedings of the American Association for Cancer Research Annual Meeting, vol. 50, pp. 300-301; Apr. 18-22, 2009.
Yukinari Kato et al.; "Evaluation of anti-podoplanin rat monoclonal antibody NZ-1 for targeting malignant gliomas" Nuclear Medicine and Biology vol. 37, No. 7, pp. 785-794, Sep. 23, 2010.
Yukinari Kato et al.; "Monoclonal Antibody Against Human Podoplanin Clone NZ-1"; Hybridoma, vol. 27, No. 4, Aug. 2008.
The extended European Search Report dated Mar. 12, 2013, which corresponds to EP Application No. 10820680.6-1403 / 2484697, International Application No. PCT/JP2010/067141 and is related to U.S. Appl. No. 13/390,284.
Yukinari Kato et al.; "Aggrus: a diagnostic marker that distinguishes seminoma from embryonal carcinoma in testicular germ cell tumors", Oncogene 23, pp. 8552-8556, Sep. 13, 2004.
Yukinari Kato et al.; "Enhanced Expression of Aggrus (T1alpha/podoplanin), a Platelet-Aggregation-Inducing Factor in Lung Squamous Cell Carcinoma", Tumor Biology, vol. 26, pp. 195-200; Jul. 7, 2005.
Kazuhiko Mishima et al.; "Increased expression of podoplanin in malignant astrocytic tumors as a novel molocular marker of malignant progression", Acta Neuropathol 111(5), pp. 483-488, Apr. 5, 2006 a.
Kazuhiko Mishima et al.; "Podoplanin expression in primary central nervous system germ cell tumors: a useful histological marker for the diagnosis of germinoma"; Acta Neuropathol. 111(6), pp. 563-568; 2006 b.
Herren Wu et al.; "Setepwise in vitro affinity maturation of Vitaxin, an axB3-specific humanized mAb"; PNAS, vol. 95, pp. 6037-6042, May 1998.
Robert Schier et al.; "Isolation of Picomolar Affinity Anti-c-erbB-2 Single-Chain Fv by Molecular Evolution of the Complementarity Determining Regions in the Center of the Antibody Binding Site"; J. Mol. Biol. 263, pp. 551-567; 1996.
Robert Schier et al.; "Isolation of High-affinity Monomeric Human Anti-c-erbB-2 Single chain Fv Using Affinity-driven Selection"; J. Mol. Biol. 255, pp. 28-43, 1996.
Wei-Ping Yang et al.; "CDR Walking Mutagenesis for the Affinity Maturation of a Potent Human Anti-HIV-1 Antibody into the Picomolar Range"; J. Mol. Biol. 254, pp. 392-403, 1995.
Frauke May et al.; "CLEC-2 is an essential platelet-activating receptor in hemostasis and thrombosis"; Blood 2009 114, pp. 3464-3472, Jul. 29, 2009.
IMGT/V-Quest Search page; http://www.imgt.org/IMGT_vquest/livret=0&Option=humanIg.

(Continued)

*Primary Examiner* — Michael Szperka
(74) *Attorney, Agent, or Firm* — Studebaker & Brackett PC

(57) ABSTRACT

Disclosed are: an anti-podoplanin antibody which has a high binding activity and a high effector activity and has low antigenicity in humans or mice; and others. Specifically disclosed are: a chimeric antibody comprising an anti-podoplanin antibody for which an epitope is a polypeptide comprising the amino acid sequence set forth in SEQ ID NO:1 (excluding rat NZ-1 antibody having a heavy chain comprising the amino acid sequence set forth in SEQ ID NO:2 and a light chain comprising the amino acid sequence set forth in SEQ ID NO:3), and a heavy chain complementarity determining region and a light chain complementary determining region of the anti-podoplanin antibody; and others.

6 Claims, 18 Drawing Sheets

(56) References Cited

OTHER PUBLICATIONS

Yukinari Kato et al.; "1. Tosa kino no kaimei to Tosa kanren Biomarker no Kaihatsu. 4) Kesshoban Gyosyu Inshi Podoplanin no Bunshi Seibutsugakuteki Kaiseki" Gene & Medicina MOOK, 2008, No. 11, pp. 165-171, 9-11.

IMGT/V-Quest Search page; http://www.imgt.org/IMGT_vquest/vquest? livret=0&Option=humanIg.

Takashi Tsuruo et al.; "Characterization of Metastatic Clones Derived from a Metastatic Variant of Mouse Colon Adenocarcinoma 26"; Cancer Research, Nov. 1983, vol. 43, pp. 5437-5442.

Minako Toyoshima et al.; "Purification and Characterization of the Platelet-Aggregating Sialoglycoprotein gp44 Expressed by Highly Metastatic Variant Cells of Mouse Colon Adenocarcinoma 26"; Cancer Research, Feb. 15, 1995, vol. 55, pp. 767-773.

Yukinari Kato et al.; "Molecular Identification of Aggrus/T1a as a Platelet Aggregation-inducing Factor Expressed in Colorectal Tumors"; The Journal of Biological Chemistry, Dec. 19, 2003, vol. 278, No. 51, pp. 51599-51605.

Mika Kato Kaneko et al.; "Conservation of a platelet activating domein of Aggrus/podoplanin as a platelet aggregation-inducing factor"; Gene, available online May 11, 2006, vol. 378, pp. 52-57.

Mika Kaneko et al.; "Functional Sialylated O-Glycan to Platelet Aggregation on Aggrus (T1a/Podoplanin) Molecules Expressed in Chinese Hamster Ovary Cells"; The Joournal of Biological Chemistry, Sep. 10, 2004, vol. 279, No. 37, pp. 38838-38843.

Yukinari Kato et al.; "Inhibition of tumor cell-induced platelet aggregation using a novel anti-podoplanin antibody reacting with its platelet-aggregation-stimulation domain"; Biochemical and Biophysical Research Communication, Sep. 7, 2006, No. 349, pp. 1301-1307.

Mika Kato Kaneko et al.; "Functional glycosylation of human podoplanin: Glycan structure of plalet aggregation-inducing factor"; Federation of European Biochemical Societies Letters 581, Jan. 5, 2007, pp. 331-336.

Katsue Suzuki-Inoue et al.; "Involvement of the Snake Toxin Receptor CLEC-2, in Podoplanin-mediated Platelet Activation, by Cancer Cells"; The Journal of Biological Chemistry; Sep. 7, 2007, vol. 282, No. 36, pp. 25993-36001.

Yukinari Kato et al.; "Molecular analysis of the pathophysiological binding of the platelet aggregation-inducing factor podoplanin to the C-type lectin-like receptor CLEC-2"; Cancer Science, Jan. 2008, vol. 99, No. 1, pp. 54-61.

Satoshi Ogasawara et al.; "Characterization of Anti-podoplanin Monoclonal Antibodies: Critical Epitopes for Neutralizing the Interaction Between Podoplanin and CLAC-2", Hybridoma, vol. 27, No. 4, pp. 259-267; 2008.

Mitsuo Satoh et al.; "The Current Stream and Prospect of Glycoscience Application—Therapeutic Antibodies-" Trends in Glycoscience and Glycotechnology, vol. 18, No. 100, pp. 129-136, Mar. 2008.

Kazuhiko Mishima et al.; "Increased expression of podoplanin in malignant astrocytic tumors as a novel molocular marker of malignant progression", Acta Neuropathol 111, pp. 483-488, Apr. 5, 2006.

Kazuhiko Mishima et al.; "Podoplanin expression in primary central nervous system germ cell tumors: a useful histological marker for the diagnosis of germinoma"; Acta Neuropathol. 111(6), pp. 563-568; 2006.

Herren Wo et al.; "Setepwise in vitro affinity maturation of Vitaxin, an axB3-specific humanized mAb"; PNAS, vol. 95, pp. 6037-6042, May 1998.

Frauke May et al.; "CLEC-2 is an essential platelet-activating receptor in hemostasis and thrombosis" ; Blood 2009 114, pp. 3464-3472, Jul. 29, 2009.

IMGT/V-Quest Search page; http://www.imgt.org/IMGT_vquest?livret=0&Option=humanIg.

Yukinari Kato et al.; "1. Tosa kino no kaimei to Tosa kanren Biomarker no Kaihatsu. 4) Kesshoban Gyosyu Inshi Podoplanin no Bunshi Seibutsugakuteki Kaiseki" Gene & Medicina MOOK, No. 11, pp. 165-171, 9-11.

Yukinari Kato et al.; "Monoclonal Antibody Against Human Podoplanin Clone NZ-1"; Hybridoma, vol. 27, No. 4, Aug. 2008, p. 323.

* cited by examiner

① NZ-1 ANTIBODY

② β-actin

Detection; ECL PLUS 1-5 EARLY LESION
6,7 EARLY LESION (Mφ)
8-11 ADVANCED LESION

ANTI-PODOPLANIN ANTIBODY, AND PHARMACEUTICAL COMPOSITION CONTAINING ANTI-PODOPLANIN ANTIBODY

TECHNICAL FIELD

The present invention relates to a novel anti-podoplanin antibody, and an anti-cancer agent containing an anti-podoplanin antibody.

BACKGROUND ART

It has been reported that platelet aggregation is induced by tumor cells in hematogenous metastasis of cancer cells. Most of cancer cells that invade into blood vessels are destroyed by an attack of the immune system of the host or by physical impact. However, it has been considered that the occurrence of platelet aggregation leads to protection of cancer cells against such a destructive process and enables metastasis of cancer cells (FIG. 13). On the other hand, it has been believed that platelet aggregation accelerates the adhesion of cancer cells to vascular endothelial cells, and the release of growth factors results in local proliferation of cancer cells. Further, capillary obstruction by clumps of platelets due to cancer cells also contributes to the acceleration of hematogenous metastasis.

By repeating experimental pulmonary metastasis of the mouse colon cancer cell line colon26, a high-metastatic strain NL-17 cell and a low-metastatic strain NL-14 cell have been established (Non-Patent Document 1). Further, a monoclonal antibody 8F11 has been constructed which exhibits high reactivity to NL-17 cells and shows low reactivity to NL-14 cells. In in vitro experiments, NL-17 cells caused platelet aggregation in mice, but such activity of NL-17 cells was inhibited by 8F11 antibodies. Further, in in vivo experiments, experimental pulmonary metastasis of NL-17 cells was inhibited by administration of 8F11 antibodies. Based on these findings, it has been suggested that NL-17 cells express a platelet-aggregating factor, which is recognized by 8F11 antibodies, to cause the aggregation of mouse platelets, consequently resulting in pulmonary metastasis. This platelet-aggregating factor was named later as "podoplanin" (also known as Aggrus).

Then, mouse podoplanin protein was purified from NL-17 cells using an 8F11 antibody column and a WGA column (Non-Patent Document 2). The purified podoplanin inhibited mouse platelet aggregation in the absence of plasma components in a concentration-dependent manner, and this aggregation reaction was completely inhibited by 8F11 antibodies.

Inventors of the present invention have now succeeded in gene cloning of podoplanin (Non-Patent Document 3). Podoplanin is a type I transmembrane protein having a C-terminal transmembrane domain. Human podoplanin, although having a low homology with mouse podoplanin, causes mouse platelet aggregation, whereas mouse podoplanin brings about platelet aggregation in a human. Through an epitope analysis of a neutralizing antibody of mouse podoplanin, 8F11 antibody, and detailed mutagenesis analyses, it has become clear that threonines (Thr) in three tandem repeats of EDxxVTPG (PLAG domain) form the active site for podoplanin-induced platelet aggregation and is conserved across species (Non-Patent Document 4). While sugar chains account for about a half of the molecular weight of podoplanin, it was determined by using glycosylation-deficient CHO mutant cells (Lec1, Lec2, Lec8) that sialic acid of an O-linked sugar chain added to Thr of the PLAG domain is the active center for platelet aggregation (Non-Patent Document 5).

Further, the present inventors have constructed a rat monoclonal antibody, NZ-1 antibody with high specificity for the purpose of purification of human podoplanin (Non-Patent Document 6). It has been seen that NZ-1 antibody is useful in Western blotting and flow cytometry as well as immunohistochemical staining, and is also utilized as an antibody having high sensitivity and specificity in immunoprecipitation. Since detailed structure analysis of sugar chain (particularly, O-linked sugar chain) using a mass spectrometer (MS) requires several tens of µg of a purified protein, screening of a cell line that expresses high level of human podoplanin was also carried out at the same time. As a result, using NZ-1 antibodies, human podoplanin was purified in large quantities from the human glioma cell line LN319 with high expression of human podoplanin (Non-Patent Document 7).

According to the detailed sugar chain structure analysis of human podoplanin, it has been elucidated that the active site for platelet aggregation of human podoplanin is a disialyl-core 1 structure added to Thr52 of a PLAG domain (Non-Patent Document 7).

Further, the present inventors have discovered that a receptor of podoplanin on platelets is CLEC-2 (C-type lectin-like receptor-2) of a C-type lectin-like receptor (Non-Patent Document 8). When Fc chimeras of CLEC-2 or membranous CLEC-2-expressing cells were constructed, specific binding between podoplanin and CLEC-2 was achieved. Further, podoplanin-induced platelet aggregation was inhibited by Fc chimeras of CLEC-2.

In addition, in order to confirm that podoplanin reacts with CLEC-2 through its PLAG domain, a variety of glycopeptides having an O-linked sugar chain added only to Thr52 of the PLAG domain were synthesized in vitro. As a result, only the glycopeptide having a disialyl-core 1 structure added to the PLAG domain exhibited high reactivity with CLEC-2 (Non-Patent Document 9).

NZ-1 antibodies inhibited binding of podoplanin to CLEC-2, and also inhibited podoplanin-induced platelet aggregation in a concentration-dependent manner. Further, tail vein injection of NZ-1 antibodies and podoplanin-expressing cells also exhibited significant inhibition of pulmonary metastasis (Non-Patent Document 9).

Further, the present inventors have synthesized 6 podoplanin Fc chimeras and 21 peptides and have confirmed that a minimal epitope of NZ-1 is AMPGAE and that 10 amino acids of GVAMPGAEDD are necessary for strong binding of podoplanin to NZ-1.

Further, anti-podoplanin antibodies (D2-40, AB3, 18H5 and rabbit polyclonal antibodies), which recognize other epitopes, did not inhibit interaction between podoplanin and CLEC-2 (Non-Patent Document 10).

From the results as above, human podoplanin has been shown to cause platelet aggregation through binding thereof to CLEC-2 and also carry out an important role in hematogenous metastasis of cancer, and thus it has been suggested that human podoplanin could be a cancer drug target.

Meanwhile, antibody pharmaceuticals using antibodies directed against disease-related targets have recently been developed. An antibody has a structure that two heavy chains (H chains) are associated with two light chains (L chains) stabilized via a pair of disulfide bonds. The heavy chain consists of a heavy-chain variable region VH, heavy-chain constant regions CH1, CH2 and CH3, and a hinge region positioned between CH1 and CH2. The light chain consists of a light-chain variable region VL and a light-chain constant region CL. Among these, a variable region fragment (Fv)

consisting of VH and VL is a region which is directly involved in antigen binding and generates the diversity of antibodies. Further, an antigen-binding region consisting of VL, CL, VH and CH1 is referred to as a Fab region, and a region consisting of a hinge region, CH2 and CH3 is referred to as an Fc region.

The action mechanism of antibody pharmaceuticals is based on two biological activities of antibodies. One of them is a target antigen-specific binding activity, which is an activity neutralizing the function of a target antigen molecule through binding thereto. Functional neutralization of the target antigen molecule is exhibited through the Fab region. As an antibody pharmaceutical taking advantage of its neutralizing activity against an antigen molecule, infliximab or bevacizumab is known.

The other is a biological activity of an antibody known as an effector activity. The effector activity is exerted as antibody-dependent cellular cytotoxicity (ADCC), complement-dependent cytotoxicity (CDC), or direct induction of apoptosis, through an Fc region of an antibody. Examples of antibody pharmaceuticals that produce efficacy utilizing their effector activity include rituximab or trastuzumab (Non-Patent Document 11).

A neutralizing activity and an effector activity are independent of each other, and it cannot be said that an antibody with one activity always has the other activity. Further, since ADCC activity or CDC activity is dependent on subclasses of an antibody, it cannot be said that the antibody, even when having ADCC activity, has CDC activity and it cannot be said that the antibody, even when having CDC activity, has ADCC activity.

As an activity of antibody pharmaceutical, particularly an effector activity is regarded as important. For example, a human Fcγ receptor IIIa has two types of polymorphism, one having a high affinity to rituximab and the other having a low affinity to rituximab. Among them superior clinical effects has been obtained in a non-Hodgkin's lymphoma patient with high-affinity polymorphism. Further, also in breast cancer therapy with trastuzumab, higher therapeutic effects are observed in a patient from whom a significantly high activity has been obtained in in vitro ADCC activity test using peripheral blood as an effector cell. These results suggest that ADCC activity is important for the development of clinically effective antibody pharmaceuticals. Accordingly, particularly regarding an anti-cancer agent, there is a need for an antibody pharmaceutical which is applicable for clinical use and exhibits a potent effector activity (Non-Patent Document 11).

As a measure of enhancing ADCC activity of an antibody, there are a method of modifying an amino acid sequence of an Fc region of an antibody and a method of controlling a structure of a sugar chain bound to an Fc region. However, such methods do not always bring about enhancement of ADCC activity. Further, even when ADCC activity is enhanced, since there is a variety of embodiments in modification of an amino acid sequence or control of a sugar chain structure, it is not easy to find a method of enhancing ADCC activity for a given antibody.

To date, podoplanin has been reported to exhibit high expression in brain tumor, mesothelioma, testicular tumor, ovarian cancer, and a variety of squamous cancers (oral cancer, pharynx cancer, larynx cancer, esophageal cancer, lung cancer, skin cancer, and uterine cervical cancer) (Non-Patent Documents 12 to 15). In particular, podoplanin is expressed in relation to malignancy in astrocytoma among brain tumors. Therefore, if there is an anti-podoplanin antibody having an effector activity such as ADCC activity or CDC activity as well as having a binding activity, it is expected that an anti-cancer action can be obtained also in such cancer.

However, as described above, with regard to NZ-1 antibody, only a platelet aggregation-neutralizing activity by the inhibition of binding of podoplanin to CLEC-2 has been confirmed hitherto, and thus involvement with hematogenous metastasis of cancer has merely been confirmed also in vivo.

Meanwhile, in research and development of antibody pharmaceuticals, immunogenicity in a human body is also a matter of concern. Monoclonal antibodies constructed with rodents such as mice or rats exhibit immunogenicity in a human body and may be contributory to attenuated effects or allergic reactions resulting from appearance of neutralizing antibodies. In order to avoid these disadvantages, a technique is being developed which renders an initial monoclonal antibody constructed using rodents into a chimeric antibody, a humanized antibody, or a fully human antibody with low antigenicity with respect to a human.

However, with regard to the method for preparing a chimeric antibody or a humanized antibody, there is no standardized method which is universally applicable to any antibody. Even when a chimeric antibody is constructed based on the antibody obtained from a different species, the resulting chimeric antibody may lose both a binding activity and an effector activity. Further, where a monoclonal antibody constructed with rodents such as mice or rats is made to be a chimeric antibody or a humanized antibody, it cannot be guaranteed that an equivalent activity can be obtained and an antibody having low antigenicity can be obtained.

As described above, regarding NZ-1 antibody, only a monoclonal antibody constructed with rats has been reported hitherto, and merely an activity of inhibiting binding of podoplanin and CLEC-2 to result in neutralization has been known for the constructed antibody. Further, an amino acid sequence of NZ-1 antibody, an amino acid sequence of a CDR or a gene sequence encoding the same has not been elucidated and there is no example specifically demonstrating a design of chimeric antibodies or the like.

PRIOR ART DOCUMENTS

Non-Patent Documents

Non-Patent Document 1: Tsuruo T., Yamori T. et al., Cancer Res. 43, 5437-5442, 1983.
Non-Patent Document 2: Toyoshima M., Nakajima M. et al., Cancer Res. 55, 767-773, 1995.
Non-Patent Document 3: Kato Y., Fujita N. et al., J. Biol. Chem. 278, 51599-51605, 2003.
Non-Patent Document 4: Kaneko MK., Kato Y. et al., Gene 378C:52-57, 2006.
Non-Patent Document 5: Kaneko M., Kato Y. et al., J. Biol. Chem. 279, 38838-38843, 2004.
Non-Patent Document 6: Kato Y., Kaneko M K. et al., Biochem. Biophys. Res. Commun., 349:1301-1307, 2006
Non-Patent Document 7: Kaneko M K., Kato Y. et al., FEBS Lett. 581, 331-336, 2007.
Non-Patent Document 8: Suzuki-Inoue K., Kato Y. et al., J. Biol. Chem. 282, 25993-26001, 2007.
Non-Patent Document 9: Kato Y., Kaneko M K. et al., Cancer Sci. 99, 54-61, 2008.
Non-Patent Document 10: Ogasawara S., et al., Hybridoma, 27(4):259-267, 2008.
Non-Patent Document 11: Satoh M. et al., Trends in Glycoscience and Glycotechnology, 18, 129-136, 2006.
Non-Patent Document 12: Kato Y., Sasagawa I. et al., Oncogene 23, 8552-8556, 2004.

Non-Patent Document 13: Kato Y., Kaneko M. et al., Tumor Biol. 26, 195-200, 2005.

Non-Patent Document 14: Mishima K., Kato Y. et al., Acta Neuropathol. 111(5):483-488, 2006a Non-Patent Document 15: Mishima K., Kato Y. et al., Acta Neuropathol. 111(6):563-568. 2006b

SUMMARY OF THE INVENTION

Problems to be Solved by the Invention

An object of the present invention is to provide an anti-podoplanin antibody which has a high binding activity and neutralizing activity as well as a high effector activity and has low antigenicity in humans or mice; and others.

Means for Solving the Problems

As a result of intensive research to address the above-mentioned problems, the inventors of the present invention have found that rat NZ-1 antibody, from which only a binding activity or a neutralizing activity was confirmed, also exhibits ADCC activity and CDC activity against podoplanin-positive tumor cells; rat NZ-1 antibody exhibits a tumor growth-inhibitory effect in a mouse tumor model; a mouse chimeric antibody using a complementarity determining region (hereinafter, also referred to as "CDR") of rat NZ-1 antibody also binds to human podoplanin; a mouse chimeric antibody exhibits ADCC activity and CDC activity against podoplanin-positive tumor cells; a human chimeric antibody using a CDR of rat NZ-1 antibody also binds to human podoplanin; a human chimeric antibody has remarkably high cellular cytotoxicity compared to the cellular cytotoxicity of rat NZ-1 antibody and a mouse chimeric antibody. The present invention has been completed based on these findings.

Specifically, the present invention relates to:

[1] Anti-podoplanin antibody for which an epitope is a polypeptide consisting of the amino acid sequence set forth in SEQ ID NO:1 (excluding rat NZ-1 antibody having a heavy chain consisting of the amino acid sequence set forth in SEQ ID NO:2 and a light chain consisting of the amino acid sequence set forth in SEQ ID NO:3);

[2] The antibody according to [1], comprising at least one of polypeptides represented by the following a) to f):

a) a heavy chain CDR1 consisting of the amino acid sequence set forth in SEQ ID NO:6;

b) a heavy chain CDR2 consisting of the amino acid sequence set forth in SEQ ID NO:7;

c) a heavy chain CDR3 consisting of the amino acid sequence set forth in SEQ ID NO:8;

d) a light chain CDR1 consisting of the amino acid sequence set forth in SEQ ID NO:9;

e) a light chain CDR2 consisting of the amino acid sequence set forth in SEQ ID NO:10; and f) a light chain CDR3 consisting of the amino acid sequence set forth in SEQ ID NO:11;

[3] The antibody according to [1], comprising at least one of polypeptides represented by the following a') to f'):

a') a heavy chain CDR1 consisting of the amino acid sequence having deletion, substitution or addition of one to several amino acids in the amino acid sequence set forth in SEQ ID NO:6, or a heavy chain CDR1 consisting of the amino acid sequence having 60% or higher identity with the amino acid sequence set forth in SEQ ID NO:6;

b') a heavy chain CDR2 consisting of the amino acid sequence having deletion, substitution or addition of one to several amino acids in the amino acid sequence set forth in SEQ ID NO:7, or a heavy chain CDR2 consisting of the amino acid sequence having 60% or higher identity with the amino acid sequence set forth in SEQ ID NO:7;

c') a heavy chain CDR3 consisting of the amino acid sequence having deletion, substitution or addition of one to several amino acids in the amino acid sequence set forth in SEQ ID NO:8, or a heavy chain CDR3 consisting of the amino acid sequence having 60% or higher identity with the amino acid sequence set forth in SEQ ID NO:8;

d') a light chain CDR1 consisting of the amino acid sequence having deletion, substitution or addition of one to several amino acids in the amino acid sequence set forth in SEQ ID NO:9, or a light chain CDR1 consisting of the amino acid sequence having 60% or higher identity with the amino acid sequence set forth in SEQ ID NO:9;

e') a light chain CDR2 consisting of the amino acid sequence having deletion, substitution or addition of one to several amino acids in the amino acid sequence set forth in SEQ ID NO:10, or a light chain CDR2 consisting of the amino acid sequence having 60% or higher identity with the amino acid sequence set forth in SEQ ID NO:10; and f') a light chain CDR3 consisting of the amino acid sequence having deletion, substitution or addition of one to several amino acids in the amino acid sequence set forth in SEQ ID NO:11, or a light chain CDR3 consisting of the amino acid sequence having 60% or higher identity with the amino acid sequence set forth in SEQ ID NO:11;

[4] The antibody according to [1], comprising the following polypeptides:

i) a heavy-chain variable region (VH) comprising the amino acid sequence set forth in SEQ ID NO:18, a heavy-chain variable region (VH) consisting of the amino acid sequence having deletion, substitution or addition of one to several amino acids in the amino acid sequence set forth in SEQ ID NO:18, or a heavy-chain variable region (VH) consisting of the amino acid sequence having 60% or higher identity with the amino acid sequence set forth in SEQ ID NO:18; and ii) a light-chain variable region (VL) set forth in SEQ ID NO:19, a light-chain variable region (VL) consisting of the amino acid sequence having deletion, substitution or addition of one to several amino acids in the amino acid sequence set forth in SEQ ID NO:19, or a light-chain variable region (VL) consisting of the amino acid sequence having 60% or higher identity with the amino acid set forth in SEQ ID NO:19;

[5] The antibody according to [4], further comprising the following polypeptides:

iii) a heavy-chain constant region 1 (CH1) consisting of the amino acid sequence set forth in SEQ ID NO:20, a heavy-chain constant region 1 (CH1) consisting of the amino acid sequence having deletion, substitution or addition of one to several amino acids in the amino acid sequence set forth in SEQ ID NO:20, or a heavy-chain constant region 1 (CH1) consisting of the amino acid sequence having 60% or higher identity with the amino acid set forth in SEQ ID NO:20; and iv) a light chain constant region (CL) consisting of the amino acid sequence set forth in SEQ ID NO:21, a light chain constant region (CL) consisting of the amino acid sequence having deletion, substitution or addition of one to several amino acids in the amino acid sequence set forth in SEQ ID NO:21, or a light chain constant region (CL) consisting of the amino acid sequence having 60% or higher identity with the amino acid sequence set forth in SEQ ID NO:21;

[6] The antibody according to any one of [1] to [5], comprising a human Fc region or a mouse Fc region;

[7] The antibody according to [6], comprising a heavy chain consisting of the amino acid sequence set forth in SEQ ID NO:23, a heavy chain consisting of the amino acid sequence having deletion, substitution or addition of one to several amino acids in the amino acid sequence set forth in SEQ ID NO:23, or a heavy chain consisting of the amino acid sequence having 60% or higher identity with the amino acid sequence set forth in SEQ ID NO:23, and a light chain consisting of the amino acid sequence set forth in SEQ ID NO:3, a light chain consisting of the amino acid sequence having deletion, substitution or addition of one to several amino acids in the amino acid sequence set forth in SEQ ID NO:3, or a light chain consisting of the amino acid sequence having 60% or higher identity with the amino acid sequence set forth in SEQ ID NO:3;

[8] The antibody according to [6], comprising a heavy chain consisting of the amino acid sequence set forth in SEQ ID NO:37, a heavy chain consisting of the amino acid sequence having deletion, substitution or addition of one to several amino acids in the amino acid sequence set forth in SEQ ID NO:37, or a heavy chain consisting of the amino acid sequence having 60% or higher identity with the amino acid sequence set forth in SEQ ID NO:37, and a light chain consisting of the amino acid sequence set forth in SEQ ID NO:39, a light chain consisting of the amino acid sequence having deletion, substitution or addition of one to several amino acids in the amino acid sequence set forth in SEQ ID NO:39, or a light chain consisting of the amino acid sequence having 60% or higher identity with the amino acid sequence set forth in SEQ ID NO:39;

[9] The antibody according to any one of [1] to [8], wherein one or more N-linked sugar chains are bound to the Fc region, and fucose is not bound to N-acetylglucosamine at the reducing end of the N-linked sugar chains;

[10] The antibody according to any one of [1] to [9], to which a substance having an anti-cancer activity is bound;

[11] DNA encoding the antibody according to any one of [1] to [9];

[12] A vector comprising DNA of [11];

[13] A transfectant comprising the vector of [12];

[14] A transfectant consisting of a cell comprising the vector of [12], wherein the activity of an enzyme involved in synthesis of GDP-fucose or an activity of α-1,6-fucosyltransferase is decreased or deficient in the cell;

[15] A method for preparing an antibody composition comprising the antibody of [9], comprising culturing the transfectant of [14], and purifying an anti-podoplanin antibody from the resulting culture;

[16] A transgenic insect comprising the vector of [12];

[17] A method for preparing an antibody composition comprising the antibody of [9], including extracting an anti-podoplanin antibody from the transgenic insect of [16] or a secretion thereof;

[18] A pharmaceutical composition comprising either of the following as an active ingredient:

(A) the antibody of any one of [1] to [9]; and (B) rat NZ-1 antibody having a heavy chain consisting of the amino acid sequence set forth in SEQ ID NO:2 and a light chain consisting of the amino acid sequence set forth in SEQ ID NO:3;

[19] The pharmaceutical composition according to [18], having an antibody-dependent cellular cytotoxicity and/or a complement-dependent cytotoxicity;

[20] The pharmaceutical composition according to [18] or [19], having an antitumor activity and/or a tumor growth-inhibitory activity;

[21] The pharmaceutical composition according to any one of [18] to [20], which is a therapeutic agent for at least one disease selected from the group consisting of podoplanin-expressing tumor, thrombosis and arteriosclerosis;

[22] The pharmaceutical composition according to [21], wherein the podoplanin-expressing tumor is at least one tumor selected from the group consisting of brain tumor, mesothelioma, testicular tumor (seminoma) and squamous cancer;

[23] A method for treating at least one disease selected from the group consisting of podoplanin-expressing tumor, thrombosis and arteriosclerosis, comprising administering any antibody of:

(A) the antibody of any one of [1] to [9]; and (B) an antibody having a heavy chain consisting of the amino acid sequence set forth in SEQ ID NO:2 and a light chain consisting of the amino acid sequence set forth in SEQ ID NO:3;

[24] A polypeptide which is any one of:

1) a polypeptide consisting of the amino acid sequence set forth in SEQ ID NO:6;

2) a polypeptide consisting of the amino acid sequence set forth in SEQ ID NO:7;

3) a polypeptide consisting of the amino acid sequence set forth in SEQ ID NO:8;

4) a polypeptide consisting of the amino acid sequence set forth in SEQ ID NO:9;

5) a polypeptide consisting of the amino acid sequence set forth in SEQ ID NO:10;

6) a polypeptide consisting of the amino acid sequence set forth in SEQ ID NO:11; and 7) a polypeptide consisting of the amino acid sequence having deletion, substitution or addition of one to several amino acids in the amino acid sequences set forth in each of SEQ ID NOs:6 to 11, or a polypeptide consisting of the amino acid sequence having 60% or higher identity with the amino acid sequence set forth in each of SEQ ID NOs:6 to 11, and which recognizes a polypeptide consisting of the amino acid sequence set forth in SEQ ID NO:1.

Advantageous Effect of the Invention

According to the present invention, an anti-podoplanin antibody having an effector activity such as ADCC activity or CDC activity can be obtained. The anti-podoplanin antibody having an effector activity is capable of specifically inhibiting not only hematogenous metastasis of cancer, but also growth of tumor cells with high expression of podoplanin. Therefore, the anti-podoplanin antibody having an effector activity is effectively used for the treatment of brain tumor, mesothelioma, testicular tumor, ovarian cancer, and a variety of squamous cancers (oral cancer, pharynx cancer, larynx cancer, esophageal cancer, lung cancer, skin cancer, and uterine cervical cancer), from each of which the expression of podoplanin is observed.

Further, the human chimeric antibody in accordance with the present invention has a remarkably high effector activity and is also considered to exhibit low antigenicity with respect to a human, and is therefore useful as a safe and highly effective pharmaceutical product.

Figure 1A:
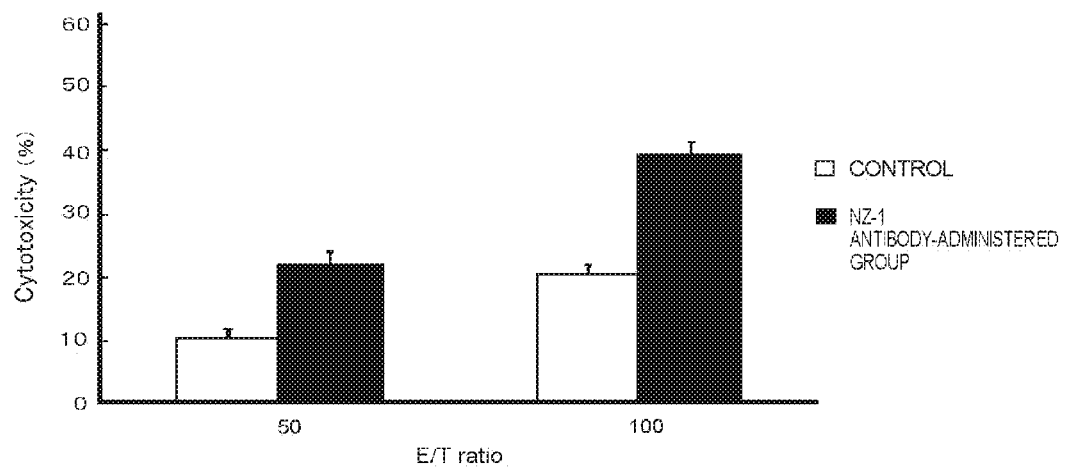
FIG. 1A illustrates the measurement results of ADCC activity of NZ-1 antibody against a mesothelioma cell (H2052 cell). ADCC activity of rat NZ-1 antibody was confirmed.

MODE FOR CARRYING OUT THE INVENTION (Anti-Podoplanin Antibody)

The present invention provides an anti-podoplanin antibody for which an epitope is a polypeptide consisting of the amino acid sequence set forth in SEQ ID NO:1 (excluding rat NZ-1 antibody having a heavy chain consisting of the amino acid sequence set forth in SEQ ID NO:2 and a light chain consisting of the amino acid sequence set forth in SEQ ID NO:3, hereinafter, also referred to as "anti-podoplanin antibody of the present invention").

The anti-podoplanin antibody of the present invention is a novel antibody, inhibits binding of podoplanin to CLEC-2, has high effector activity such ADCC activity or CDC activity, and has a tumor growth-inhibitory potency (which will be described hereinafter).

There has been known hitherto that rat NZ-1 antibody having a heavy chain consisting of the amino acid sequence set forth in SEQ ID NO:2 and a light chain consisting of the amino acid sequence set forth in SEQ ID NO:3 inhibits binding of podoplanin to CLEC-2 and as a result, is capable of inhibiting hematogenous metastasis. However, an antibody having a binding-inhibitory activity and a high effector activity at the same time is rare, and it could not have been foreseen by those skilled in the art that the anti-podoplanin antibody of the present invention exhibits a binding-inhibitory activity between podoplanin and CLEC-2 and also shows an effector activity.

As used herein, the term "polypeptide consisting of the amino acid sequence set forth in SEQ ID NO:1" is a minimal epitope which is on podoplanin and is recognized by rat NZ-1 antibody (Non-Patent Document 10).

The anti-podoplanin antibody of the present invention preferably includes at least one of heavy chain complementarity determining regions (heavy chain CDR1 to heavy chain CDR3) as shown in (1) to (3) below, and light chain complementarity determining regions (light chain CDR1 to light chain CDR3) as shown in (4) to (6). These heavy chain CDRs and light chain CDRs were first determined at this time by the present inventors, based on the rat NZ-1 antibody.

(1) a heavy chain CDR1 consisting of the amino acid sequence set forth in SEQ ID NO:6, a heavy chain CDR1 consisting of the amino acid sequence having deletion, substitution or addition of one to several amino acids in the amino acid sequence set forth in SEQ ID NO:6, or a heavy chain CDR1 consisting of the amino acid sequence having 60% or higher identity with the amino acid sequence set forth in SEQ ID NO:6, (2) a heavy chain CDR2 consisting of the amino acid sequence set forth in SEQ ID NO:7, a heavy chain CDR2 consisting of the amino acid sequence having deletion, substitution or addition of one to several amino acids in the amino acid sequence set forth in SEQ ID NO:7, or a heavy chain CDR2 consisting of the amino acid sequence having 60% or higher identity with the amino acid sequence set forth in SEQ ID NO:7, (3) a heavy chain CDR3 consisting of the amino acid sequence set forth in SEQ ID NO:8, a heavy chain CDR3 consisting of the amino acid sequence having deletion, substitution or addition of one to several amino acids in the amino acid sequence set forth in SEQ ID NO:8, or a heavy chain CDR3 consisting of the amino acid sequence having 60% or higher identity with the amino acid sequence set forth in SEQ ID NO:8, (4) a light chain CDR1 consisting of the amino acid sequence set forth in SEQ ID NO:9, a light chain CDR1 consisting of the amino acid sequence having deletion, substitution or addition of one to several amino acids in the amino acid sequence set forth in SEQ ID NO:9, or a light chain CDR1 consisting of the amino acid sequence having 60% or higher identity with the amino acid sequence set forth in SEQ ID NO:9, (5) a light chain CDR2 consisting of the amino acid sequence set forth in SEQ ID NO:10, a light chain CDR2 consisting of the amino acid sequence having deletion, substitution or addition of one to several amino acids in the amino acid sequence set forth in SEQ ID NO:10, or a light chain CDR2 consisting of the amino acid sequence having 60% or higher identity with the amino acid sequence set forth in SEQ ID NO:10, (6) a light chain CDR3 consisting of the amino acid sequence set forth in SEQ ID NO:11, a light chain CDR3 consisting of the amino acid sequence having deletion, substitution or addition of one to several amino acids in the amino acid sequence set forth in SEQ ID NO:11, or a light chain CDR3 consisting of the amino acid sequence having 60% or higher identity with the amino acid sequence set forth in SEQ ID NO:11.

The anti-podoplanin antibody of the present invention may include any numbers of the said heavy chain CDRs and light chain CDRs as long as the effect of the present invention is achieved, and preferably includes 3 or a higher number of the said heavy chain CDRs and light chain CDRs, more preferably 5 or a higher number of the said heavy chain CDRs and light chain CDRs, and most preferably 6 of the said heavy chain CDRs and light chain CDRs.

As the anti-podoplanin antibody of the present invention, an antibody having the following combination of the heavy chain CDRs and light chain CDRs is preferably used.

a) a CDR1 consisting of the amino acid sequence set forth in SEQ ID NO:6;
b) a CDR2 consisting of the amino acid sequence set forth in SEQ ID NO:7;
c) a CDR3 consisting of the amino acid sequence set forth in SEQ ID NO:8;
d) a CDR1 consisting of the amino acid sequence set forth in SEQ ID NO:9;
e) a CDR2 consisting of the amino acid sequence set forth in SEQ ID NO:10; and
f) a CDR3 consisting of the amino acid sequence set forth in SEQ ID NO:11.

As used herein, the term, "amino acid" is used in the broadest sense and includes naturally-occurring amino acids and non-naturally-occurring amino acids such as amino acid variants and derivatives. Taking into consideration this broad definition, those skilled in the art will appreciate that examples of the amino acids as used herein include naturally-occurring proteinaceous L-amino acids; D-amino acids; chemically modified amino acids such as amino acid variants and derivatives; naturally-occurring non-proteinaceous amino acids such as norleucine, β-alanine, and ornithine; and chemically synthesized compounds having properties known to be those of amino acids in the art. Examples of non-naturally-occurring amino acids include α-methylamino acid (α-methylalanine, or the like), D-amino acid, histidine-like amino acid (2-amino-histidine, β-hydroxy-histidine, homo-histidine, α-fluoromethyl-histidine, α-methyl-histidine, or the like), amino acids having extra methylene in a side chain ("homo" amino acid) and amino acids in which carboxy-functional amino acid in a side chain is substituted with a sulfonate group (cysteic acid, or the like).

As used herein, the term "polypeptide" means a molecule in which amino acids are connected by a peptide bond, and includes naturally-occurring or artificial proteins, and protein fragments.

As used herein, when the expression "having deletion, substitution or addition of one to several amino acids" is used, the number of amino acids that is deleted, substituted or the like is not particularly limited as long as the resulting polypeptide retains a function as a CDR. The number of amino acids that is deleted, substituted or the like is 1 to 4, preferably 1 to 3, and more preferably 1 to 2, or is within 20% of the total length of the polypeptide, and preferably within 10%. The amino acid to be substituted or added may be a naturally-occurring amino acid, a non-naturally-occurring amino acid or an amino acid analog, and preferably a naturally-occurring amino acid. The position of deletion, substitution or addition may be any site of an original polypeptide, as long as the function as a CDR is retained.

As used herein, the term "having 60% or higher identity with the amino acid sequence set forth in SEQ ID NO:X" means that, when two polypeptides are aligned to result in maximum identity of amino acid sequences therebetween, the ratio of the number of amino acid residues being common therebetween to the total number of amino acids set forth in SEQ ID NO:X is 60% or higher. The CDR of the present invention also includes a polypeptide consisting of the amino acid sequence having 60% or higher, preferably 70% or higher, further preferably 80% or higher identity, with each of the amino acid sequences set forth in SEQ ID NOs:6 to 11. Such a polypeptide also retains the function as a CDR.

A CDR consisting of the amino acid sequence having deletion, substitution or addition of one to several amino acids in the amino acid sequence set forth in one of SEQ ID NOs:6 to 11, or a CDR consisting of the amino acid sequence having 60% or higher identity to the amino acid sequence set forth in any one of SEQ ID NOs:6 to 11 may be prepared by using a known method such as site-directed mutagenesis, random mutagenesis, chain shuffling, or CDR walking. According to such a method, it is well known to those skilled in the art that CDRs with more mature affinity may be obtained by presenting an antibody or antibody fragment having a variety of variations in CDRs on the phage surface by a phage display method, followed by screening using an antigen (e.g., Wu et al., PNAS, 95:6037-6042 (1998); Schier, R. et al., J. Mol. Bio. 263:551-567 (1996); Schier, R. et al., J. Mol. Biol. 255:28-43 (1996); Yang, W. P. et al., J. Mol. Biol., 254:392-403 (1995).).

The antibody according to the present invention may be a recombinant antibody, a monoclonal antibody, a polyclonal antibody, or the like.

Further, the anti-podoplanin antibody of the present invention may be any isotype of IgG, IgM, IgA, IgD and IgE. Preferred is IgG.

The anti-podoplanin antibody of the present invention includes, but is not limited to, low-molecular weight antibodies such as a Fab fragment, a F(ab')$_2$ fragment, an Fv fragment, and an scFv fragment, in addition to a mouse chimeric antibody, a human chimeric antibody, and a humanized antibody, as long as it recognizes an epitope consisting of the amino acid sequence set forth in SEQ ID NO:1.

As used herein, the term "chimeric antibody" or "chimera-type antibody" refers to an antibody consisting of antibody fragments derived from different species.

The chimeric antibody which is preferable as the anti-podoplanin antibody of the present invention is a mouse chimeric antibody or a human chimeric antibody. The former has a variable region which recognizes an epitope consisting of the amino acid sequence set forth in SEQ ID NO:1 and a mouse-derived Fc region, whereas the latter recognizes the same epitope and comprises a human-derived Fc region. Included in the variable region which recognizes an epitope consisting of the amino acid sequence set forth in SEQ ID NO:1 are preferably the foregoing heavy chain CDR1 to 3 and light chain CDR1 to 3. Other regions, i.e., heavy chain framework regions (FR) 1 to 4 and light chain FR1 to 4 may be derived from any species.

Examples of the mouse chimeric antibody of the present invention include:

(1) an antibody including a Fab region of rat NZ-1 antibody and an Fc region of a mouse antibody;

(2) an antibody including VH and VL regions of rat NZ-1 antibody and CH1, CL, hinge region, CH2, and CH3 of a mouse antibody;

(3) an antibody having the foregoing heavy chain CDR1 to 3 and light chain CDR1 to 3, with all of other regions, including 4 framework regions (FRs) of a heavy chain and a light chain, being derived from a mouse antibody; and others.

Further, the mouse chimeric antibody of the present invention is preferably a chimeric antibody with a mouse IgG2a subclass which is generally referred to as being potent in terms of ADCC activity.

The mouse chimeric antibody of the present invention preferably contains a Fab region of rat NZ-1 antibody and an Fc region of a mouse antibody. Particularly preferred is a mouse chimeric antibody having a heavy chain consisting of the amino acid sequence set forth in SEQ ID NO:23; a heavy chain consisting of the amino acid sequence having deletion, substitution or addition of one to several amino acids in the amino acid sequence set forth in SEQ ID NO:23; or a heavy chain consisting of the amino acid sequence having 60% or higher identity to the amino acid sequence set forth in SEQ ID NO:23; and a light chain consisting of the amino acid sequence set forth in SEQ ID NO:3; a light chain consisting of the amino acid sequence having deletion, substitution or addition of one to several amino acids in the amino acid sequence set forth in SEQ ID NO:3, or a light chain consisting of the amino acid sequence having 60% or higher identity to the amino acid sequence set forth in SEQ ID NO:3.

Among them, a mouse chimeric antibody comprising a heavy chain consisting of the amino acid sequence set forth in SEQ ID NO:23 and a light chain consisting of the amino acid sequence set forth in SEQ ID NO:3 is preferable.

This mouse chimeric antibody adopts a mouse IgG2a Fc, and was observed to exhibit ADCC activity and CDC activity against podoplanin-positive human tumor cells, as described in Examples.

Examples of the human chimeric antibody of the present invention include:

(1) an antibody including a Fab region of rat NZ-1 antibody and an Fc region of a human antibody; and (2) an antibody having VH and VL regions of rat NZ-1 antibody and CH1, CL, hinge region and CH2, CH3 of a human antibody.

Further, the human chimeric antibody of the present invention is preferably a chimeric antibody with a human IgG1 subclass which is generally known to have high ADCC activity.

The human chimeric antibody of the present invention preferably contains VH and VL regions of rat NZ-1 antibody and CH1, CL, hinge region, CH2, and CH3 of a human antibody.

Particularly preferred is a mouse chimeric antibody comprising a heavy chain consisting of the amino acid sequence set forth in SEQ ID NO:37, a heavy chain consisting of the amino acid sequence having deletion, substitution or addition of one to several amino acids in the amino acid sequence set forth in SEQ ID NO:37, or a heavy chain consisting of the amino acid sequence having 60% or higher identity to the amino acid sequence set forth in SEQ ID NO:37, and a light chain consisting of the amino acid sequence set forth in SEQ ID NO:39, a light chain consisting of the amino acid sequence having deletion, substitution or addition of one to several amino acids in the amino acid sequence set forth in SEQ ID NO:39, or a light chain consisting of the amino acid sequence having 60% or higher identity to the amino acid sequence set forth in SEQ ID NO:39.

Among them, a human chimeric antibody comprising a heavy chain consisting of the amino acid sequence set forth in SEQ ID NO:37 and a light chain consisting of the amino acid sequence set forth in SEQ ID NO:39 is preferable.

This human chimeric antibody is a chimeric antibody with a human IgG1 subclass, and was confirmed to exhibit a remarkably higher ADCC activity and CDC activity, as compared to rat NZ-1 antibody or a mouse chimeric antibody, against podoplanin-positive human tumor cells, as described in Examples.

As used herein, the term "humanized antibody" refers to a human antibody in which an amino acid sequence characteristic to a non-human-derived antibody occupies the corresponding site. Examples of the humanized antibody include an antibody having the foregoing heavy chain CDR1 to 3 and light chain CDR1 to 3, with all of other regions, including 4 framework regions (FRs) of a heavy chain and a light chain, being derived from a human antibody, and others. Such an antibody may also be referred to as a CDR-grafted antibody. The term "humanized antibody" may include a human chimeric antibody.

As used herein, the term "low-molecular weight antibody" refers to a fragment of an antibody or an entity in which any molecule is bound to a fragment of an antibody and which recognizes the same epitope as that of an original antibody. Specific examples of the low-molecular weight antibody include, but are not limited to, Fab consisting of VL, VH, CL and CH1 regions; F(ab')$_2$ in which two Fabs are connected in a hinge region via a disulfide bond; Fv consisting of VL and VH; a single-chain antibody scFv in which VL and VH are connected via an artificial polypeptide linker; and a bispecific antibody such as diabody, an scDb, a tandem scFv, and a leucine zipper.

The low-molecular weight antibody, which is preferable as the anti-podoplanin antibody of the present invention, is a low-molecular weight antibody containing the foregoing heavy chain CDR1 to 3 and light chain CDR1 to 3.

The "antibody" as used herein also includes an antibody with modification such as glycosylation. Examples of such an antibody include antibodies in which one or more N-linked sugar chains are bound to an Fc region, and fucose is not bound to N-acetylglucosamine of reducing ends of the N-linked sugar chains.

For example, two binding sites of an N-linked sugar chain are present in the Fc region of an IgG antibody, and complex-type sugar chains are bound to these sites. The "N-linked sugar chain" refers to a sugar chain which is bound to Asn of the Asn-X-Ser/Thr sequence, and has a common structure of Man$_3$GlcNAc$_2$-Asn. Depending on the kind of sugar chains bound to two mannoses (Man) at the non-reducing end, the "N-linked sugar chain" is classified into a high mannose type, a hybrid type, and a complex type.

Although fucose is capable of binding to N-acetylglucosamine (GlcNAc) at the reducing end of an N-linked sugar chain, it is known that when fucose is not bound, ADCC activity is remarkably increased as compared to when fucose is bound. This is disclosed in, for example, the pamphlet of WO2002/031140, the disclosure of which is incorporated by reference herein in its entirety.

Since a remarkable increase in ADCC activity may lead to a reduction of the dose when an antibody is used as a medicine, adverse side effects may be reduced and medical expenses may also be curtailed.

Further, the present invention also includes the anti-podoplanin antibody of the present invention to which a substance having an anti-cancer activity is linked.

As used herein, the term "substance having an anti-cancer activity" refers to a substance which brings about at least one of: reduction of a tumor size (retardation or stopping), inhibition of tumor metastasis, inhibition of tumor growth (retardation or stopping), and alleviation of one or plural symptoms associated with cancer. Specific examples thereof include, but are not limited to, a toxin, an anti-cancer agent, and a radioisotope.

Examples of the toxin having an anti-cancer activity include *Pseudomonas* exotoxin (PE) A or a cytotoxic fragment thereof (for example, PE38), a diphtheria toxin, and ricin A. The toxin having an anti-cancer activity exhibits toxicity only against cells to which a toxin together with an anti-podoplanin antibody is introduced, that is, cancer cells expressing podoplanin, and is therefore advantageous from the viewpoint of being capable of obtaining specific effects without having adverse effects on surrounding cells.

Examples of the anti-cancer agent include low-molecular weight compounds such as adriamycin, daunomycin, mitomycin, cisplatin, vincristine, epirubicin, methotrexate, 5-fluorouracil, aclacinomycin, nitrogen mustards, cyclophosphamide, bleomycin, daunorubicin, doxorubicin, vincristine, vinblastine, vindesine, tamoxifen, and dexamethasone, and proteins such as cytokines activating immunocompetent cells (for example, human interleukin 2, human granulocyte-macrophage colony-stimulating factor, human macrophage colony-stimulating factor, and human interleukin 12).

Examples of the radioisotope having an anti-cancer activity include $^{32}P$, $^{14}C$, $^{125}I$, $^{3}H$, $^{131}I$, $^{211}At$, and $^{90}Y$. A radioisotope also exhibits toxicity against cells to which an anti-podoplanin antibody binds, that is, cells around podoplanin-expressing cells. Generally, since tumor cells are not uniform and not every tumor cell expresses podoplanin, radioisotopes are useful to kill the surrounding podoplanin-negative tumor cells. Further, where a radioisotope is bound, the anti-podoplanin antibody is preferably a low-molecular weight antibody such as Fab or scFv.

The substance having an anti-cancer activity may be directly linked to an anti-podoplanin antibody by a known method. Further, for example, after being enclosed in a carrier such as liposome, the substance having an anti-cancer activity may be linked to an anti-podoplanin antibody.

Where the substance having an anti-cancer activity is a protein or a polypeptide, the substance having an anti-cancer activity may be expressed in the form of a fusion protein of a substance having an anti-cancer activity and an anti-podoplanin antibody by linking DNA encoding the anti-podoplanin antibody of the present invention and DNA encoding the substance having an anti-cancer activity, followed by insertion thereof into a suitable expression vector.

(DNA Encoding Anti-Podoplanin Antibody)

Further, the present invention includes DNA encoding the anti-podoplanin antibody of the present invention. Such DNA may be sequenced according to a known method by those skilled in the art and may be prepared by a known method.

Where the anti-podoplanin antibody of the present invention is an antibody containing the foregoing heavy chain CDR1 to 3 and light chain CDR1 to 3, DNA encoding the anti-podoplanin antibody of the present invention includes DNA encoding heavy chain CDR1 to 3 including base sequences set forth in SEQ ID NOs:12 to 14, respectively, and DNA encoding light chain CDR1 to 3 including base sequences set forth in SEQ ID NOs:15 to 17, respectively.

For example, description is made of the case where the anti-podoplanin antibody of the present invention is a mouse chimeric antibody having a heavy chain consisting of the amino acid sequence set forth in SEQ ID NO:23, and a light chain consisting of the amino acid sequence set forth in SEQ ID NO:3.

VH and CH1, and VL and CL of the mouse chimeric antibody are derived from rat NZ-1 antibody. DNA encoding them may be obtained, for example, by preparing total RNA from a hybridoma that produces rat NZ-1 antibody using a standard technique, preparing mRNA encoding an NZ-1 antibody using a commercial kit, and synthesizing cDNAs of VH, CH1, VL and CL regions from the mRNA using reverse transcriptase, followed by PCR amplification. Meanwhile, a hinge region, CH2 and CH3 are derived from a mouse, and DNA encoding them may be obtained in the same manner as above.

Next, a full-length light chain gene may be obtained by operatively linking DNA encoding VL and DNA encoding CL. Further, a full-length heavy chain gene may be obtained by operatively linking DNA encoding VH, CH1, hinge region, CH2 and CH3, and thus, DNA encoding a mouse chimeric antibody may obtained by combining these.

The base sequence of DNA encoding a heavy chain consisting of the amino acid sequence set forth in SEQ ID NO:23 is set forth in SEQ ID NO:24, and the base sequence of DNA encoding a light chain consisting of the amino acid sequence set forth in SEQ ID NO:3 is set forth in SEQ ID NO:5.

Further, where the anti-podoplanin antibody of the present invention is scFv, DNA encoding the same may be obtained by operatively linking DNA encoding VH and VL to DNA encoding a linker peptide.

Further, where the anti-podoplanin antibody of the present invention is a humanized antibody, DNA encoding the same may be obtained in such a manner that DNA designed for the connection of the foregoing heavy chain CDR1 to 3 and light chain CDR1 to 3 to a framework region of a human antibody is synthesized by a PCR method from several oligonucleotides constructed to have terminally overlapping parts, followed by linking thereof to DNA encoding a human antibody constant region.

(Vector)

The present invention includes a vector containing DNA encoding the anti-podoplanin antibody of the present invention. The expression vector may be appropriately selected according to a host cell to be used, and examples thereof include a plasmid, a retrovirus, an adenovirus, an adeno-associated virus (AAV), a plant virus such as cauliflower mosaic virus or tobacco mosaic virus, a cosmid, a YAC, and an EBV-derived episome. Into these expression vectors, DNA encoding the anti-podoplanin antibody of the present invention may be inserted by a known method (such as by a method using restriction enzymes).

Further, the vector of the present invention may also contain a promoter for controlling the expression of an antibody gene, a replication origin, a selection marker gene, and the like. The promoter and replication origin may be appropriately selected depending on the nature of host cell and vector.

(Transfectant)

The present invention includes a transfectant containing the vector of the present invention. The transfectant may be obtained by transfecting the vector of the present invention into a suitable host cell. Examples of the host cell that can be used in the present invention include a eukaryotic cell such as a mammalian cell (CHO cell, COS cell, myeloma cell, HeLa cell, Vero cell, or the like), an insect cell, a plant cell, or a fungus cell (*Saccharomyces, Aspergillus*, or the like), and a prokaryotic cell such as *Escherichia coli* (*E. coli*) or *Bacillus subtilis*.

(Production of Anti-Podoplanin Antibody of the Present Invention)

There is no limitation on the method of producing the anti-podoplanin antibody of the present invention. For example, the anti-podoplanin antibody of the present invention may be produced by culturing the foregoing transfectant of the present invention under proper conditions to express an antibody, and isolating and purifying the expressed antibody by using a known method. Specifically, isolation and purification of an antibody may be carried out by appropriate combination of an affinity column using protein A or the like, other chromatography columns, filters, ultrafiltration, salting-out, dialysis, and the like.

Further, where the anti-podoplanin antibody of the present invention is a low-molecular weight antibody, expression of the antibody may be made according to the above method, using DNA encoding the low-molecular weight antibody. Alternatively, the anti-podoplanin antibody of the present invention may be produced by treating an antibody with an enzyme such as papain or pepsin.

The antibody according to the present invention may be different in terms of an amino acid sequence, a molecular weight, an isoelectric point, presence/absence of sugar chains, conformation or the like, depending on the production process or purification method. However, the resulting antibody is included within the present invention as long as it has the function equal to that of the antibody of the present invention. For example, when the antibody of the present invention is expressed in a prokaryotic cell such as *E. coli*, a methionine residue is added to the N-terminus of an amino acid sequence of an original antibody. The present invention also encompasses such an antibody.

An antibody having an N-linked sugar chain with no binding of fucose to N-acetylglucosamine of the reducing end thereof may be prepared by a known method or a method analogous thereto. Such a method for preparing an antibody is described in, for example, the pamphlet of WO2002/031140 or JP2009-225781 A, the disclosure of which is incorporated by reference herein in its entirety.

Specifically, for example, the said antibody having no fucose bound to the reducing end N-acetylglucosamine may be obtained by transforming a cell where an activity of an enzyme involved in synthesis of GDP-fucose or an activity of α-1,6-fucosyltransferase is decreased or deficient, using a vector containing DNA encoding the anti-podoplanin antibody in accordance with the present invention, culturing the resulting transfectant, and then purifying a desired anti-podoplanin antibody.

Examples of the enzyme involved in synthesis of GDP-fucose include GDP-mannose 4,6-dehydratase (GMP), GDP-keto-6-deoxymannose 3,5-epimerase, 4-reductase (Fx), and GDP-beta-L-fucose pyrophosphorylase (GFPP).

Here, the cell is not particularly limited, but is preferably a mammalian cell. For example, a CHO cell may be used which is attenuated or deficient in terms of the above-mentioned enzymatic activity.

Although the antibody composition obtained by the above method may contain an antibody having fucose bound to N-acetylglucosamine of the reducing end, a fraction of the fucose-bound antibody is 20% by weight or less of the total antibody, preferably 10% by weight or less, more preferably 5% by weight or less, and most preferably 3% by weight or less.

Further, the antibody having an N-linked sugar chain with no binding of fucose to N-acetylglucosamine at the reducing end thereof may be obtained by introducing a vector containing DNA encoding the anti-podoplanin antibody in accordance with the present invention into an insect egg, followed by incubation to grow the insect and optionally crossbreeding to construct a transgenic insect, and extracting an anti-podoplanin antibody from the transgenic insect or a secretion thereof. As the insect, a silkworm may be used. In such a case, the antibody may be extracted from silkworm cocoons.

Although the antibody composition obtained according to this method may also contain an antibody having fucose bound to N-acetylglucosamine of the reducing end, a fraction of the fucose-bound antibody is 20% by weight or less of the total antibody, preferably 10% by weight or less, more preferably 5% by weight or less, and most preferably 3% by weight or less.

(Activity of Antibody of the Present Invention)

The present inventors have discovered that the anti-podoplanin antibody of the present invention, and rat NZ-1 antibody having a heavy chain consisting of the amino acid sequence set forth in SEQ ID NO:2 and a light chain consisting of the amino acid sequence set forth in SEQ ID NO:3 (hereinafter, also referred to as "antibody of the present invention" collectively) have an effector activity such as ADCC activity or CDC activity as well as a binding-inhibitory activity against binding of podoplanin to CLEC-2, and also exhibit a tumor growth-inhibitory activity. These activities may be measured in the following manner.

(1) Binding Activity

The binding activity of an antibody may be measured by a known method, for example, ELISA (enzyme-linked immunosorbent assay), EIA (enzyme immunoassay), RIA (radioimmunoassay), a fluorescent antibody method, or an FACS method.

(2) ADCC Activity

The ADCC activity refers to a cytotoxic activity that an Fcγ receptor-bearing cell (effector cell) exerts against a target cell, when the antibody of the present invention is bound to a cell surface antigen of the target cell, by binding to the Fc region of the antibody through its Fcγ receptor.

The ADCC activity may be determined by mixing podoplanin-expressing target cells, effector cells, and the antibody of the present invention, and measuring the strength of ADCC. As the effector cells, for example, mouse splenocytes, or monocytes isolated from human peripheral blood or bone marrow may be used. As the target cells, for example, podoplanin-positive mesothelioma cells or podoplanin-positive glioma cells may be used. The target cell is labeled with $^{51}$Cr or the like in advance, the antibody of the present invention is added thereto, followed by incubation, and then an appropriate ratio of an effector cells relative to the target cells is added, followed by incubation. After incubation is completed, the supernatant is collected and the label in the supernatant is counted. In this manner, the ADCC activity may be measured.

(3) CDC Activity

The CDC activity refers to cellular cytotoxicity caused by the complement system.

The CDC activity may be measured by using a complements in place of an effector cells in the test of ADCC activity.

(4) Tumor Growth-Inhibitory Activity

The tumor growth-inhibitory activity may be measured by using tumor-bearing model animals. For example, a tumor is subcutaneously implanted into a mouse, and the antibody of the present invention is subsequently administered to the animal. A tumor growth-inhibitory effect may be measured by comparing volumes of tumor tissue between the non-administered group and the administered group.

The tumor growth-inhibitory activity of the present invention may be a result of inhibition of growth of individual cells or may be a result of induction of cell death.

(Pharmaceutical Composition)

The present inventors have discovered that the antibody of the present invention has, in addition to a binding-inhibitory activity against binding of podoplanin to CLEC-2 which has been known for rat NZ-1 antibody, an effector activity such as ADCC activity or CDC activity and a tumor growth-inhibitory activity. Accordingly, the antibody of the present invention is effective in therapy of cancer expressing a podoplanin. The pharmaceutical composition of the present invention contains the antibody of the present invention, and pharmaceutically acceptable carriers or additives.

Examples of carriers and additives include, but are not limited to, water, saline, phosphate buffer, dextrose, a pharmaceutically acceptable organic solvent such as glycerol or ethanol, collagen, polyvinyl alcohol, polyvinylpyrrolidone, a carboxy vinyl polymer, carboxymethylcellulose sodium, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, Vaseline, paraffin, stearyl alcohol, stearic acid, human serum albumin, mannitol, sorbitol, lactose, and a surfactant.

The pharmaceutical composition of the present invention may be provided in a variety of forms, for example, a solution (for example, an injection), a dispersion, a suspension, a tablet, a pill, a powder, or a suppository. A preferred embodiment is an injection, and parenteral administration (for example, intravenously, transdermally, intraperitoneally, or intramuscularly) is preferable.

The pharmaceutical composition of the present invention is therapeutically effective for podoplanin-related diseases, for example, tumor, thrombosis, or arteriosclerosis.

As described above, it has been suggested that podoplanin causes platelet aggregation through binding thereof to CLEC-2. Further, there have been reports that CLEC-2, which is a receptor of podoplanin on platelets, is involved in thrombosis/arteriosclerosis, specifically, CLEC-2-deficient platelets exhibit a poor aggregation capacity both in vitro and in vivo, and deletion of CLEC-2 results in prolongation of the bleeding time, thereby preventing occlusive arterial thrombus formation (May, F. et al., Blood prepublished online Jul. 29, 2009; doi:10.1182/blood-2009-05-222273).

Further, as described in Examples of the present specification, high expression of podoplanin in an arteriosclerotic lesion was also found. From these facts, it is strongly suggested that the pharmaceutical composition of the present invention is therapeutically effective for thrombosis or arteriosclerosis.

Meanwhile, examples of podoplanin-related tumor include brain tumor, mesothelioma, testicular tumor, ovarian cancer, and squamous cancer. Here, squamous cancer includes, but is not limited to, oral cancer, pharynx cancer, larynx cancer, esophageal cancer, lung cancer, skin cancer, and uterine cervical cancer.

The present invention also includes a method for the treatment of a podoplanin-related disease, including administering a therapeutically effective amount of the antibody of the present invention.

As used herein, the term "therapeutically effective amount" refers to an amount of the agent which brings about the alleviation of one or plural symptoms of the disease being treated to a certain extent. For an anti-cancer agent, the therapeutically effective amount means an amount which brings about at least one of: reduction of a tumor size; inhibition of tumor metastasis (retardation or stopping); inhibition of tumor growth (retardation or stopping), and alleviation of one or plural symptoms associated with cancer.

Specifically, the dose of the antibody of the present invention may be in a range of, for example, 0.025 to 50 mg/kg, preferably 0.1 to 50 mg/kg, more preferably 0.1 to 25 mg/kg, and even more preferably 0.1 to 10 mg/kg or 0.1 to 3 mg/kg, but is not limited thereto.

(Markers and Diagnostic Agents)

As described above, podoplanin exhibits high expression in a certain tumor cell. Therefore, the antibody of the present invention is useful in the diagnosis of cancer, particularly of cancer with high expression of podoplanin, such as brain tumor, mesothelioma, testicular tumor, ovarian cancer, and a variety of squamous cancers (oral cancer, pharynx cancer, larynx cancer, esophageal cancer, lung cancer, skin cancer, and uterine cervical cancer).

Further, as described in Examples, high expression of podoplanin in an arteriosclerotic lesion was confirmed by Western blotting using rat NZ-1 antibody. Accordingly, the anti-podoplanin antibody of the present invention is also useful in the diagnosis of arteriosclerosis.

In arteriosclerotic lesion, high expression of podoplanin was observed in a macrophage-exuding lesion out of early lesions. Since the macrophage-exuding lesion has been known as readily leading to an advanced lesion, early detection of arteriosclerosis as readily leading to an advanced lesion is expected by a diagnostic method through the detection of podoplanin.

From these, the present invention also includes a diagnostic agent of cancer or arteriosclerosis containing the antibody of the present invention, use of an antibody for the diagnosis of cancer or arteriosclerosis, and a diagnostic method of cancer or arteriosclerosis using the antibody of the present invention.

EXAMPLES

1. Amino Acid Sequencing of Rat NZ-1 Antibody and Base Sequencing of Rat NZ-1 Antibody Gene Total RNA was extracted from $1 \times 10^6$ NZ-1 hybridoma cells (see Non-Patent Document 6) using a QIAGEN RNeasy mini kit.

Synthesis of cDNA was carried out from 1 μg of total RNA using a SuperScript III First-Strand Syntheses kit. The cDNA was used as a template in the following experiment. Amplification of H chain was carried out using the following primers.

S1: tcctcacc atg gac ttc agg (SEQ ID NO:25)

AS1: tca ttt acc agg aga gtg gg (SEQ ID NO:26)

PCR was carried out using a QIAGEN HotStar Taq. The temperature conditions were set as follows: 35 cycles of 95° C. for 15 minutes, 94° C. for 30 seconds, 50° C. for 30 seconds, and 72° C. for 1 minute, and finally 72° C. for 10 minutes.

The PCR amplification product was purified using a QIAGEN PCR purification kit, subcloned using a pcDNA3-topo cloning kit, and determination of the base sequence was carried out from the vector primer.

Amplification of L chain was carried out using the following primers.

```
                                            (SEQ ID NO: 27)
BamHI-S1:    cca ggatcc acc atg aca tgg act cta ct (SEQ ID NO: 28)
EcoRI-AS1:   ggt gaattc cta gac aca ttc tgc agg ag
```

PCR was carried out using a QIAGEN HotStar Taq. The temperature conditions were set as follows: 35 cycles of 95° C. for 15 minutes, 94° C. for 30 seconds, 53° C. for 30 seconds, and 72° C. for 1 minute, and finally 10 minutes at 72° C.

The PCR amplification product was purified using a QIAGEN PCR purification kit, and treated with restriction enzymes BamHI and EcoRI at 37° C. for one hour. The restriction enzyme-treated PCR product was purified in Wizard SV Gel&PCR Clean up systems, and subcloned into vectors pcDNA3.1/Zeocin or pcDNA3 (G418) treated with the same enzymes, followed by confirmation of the base sequence from the vector primer. The base sequence of DNA encoding H chain is as set forth in SEQ ID NO:4, and the base sequence of DNA encoding L chain is as set forth in SEQ ID NO:5.

The amino acid sequence was predicted from the base sequence. The H chain amino acid sequence is as set forth in SEQ ID NO:2, and the L chain amino acid sequence is as set forth in SEQ ID NO:3.

2. Sequencing of CDR

The CDR regions were specified from the determined base sequence using sequence prediction software of immunoglobulins described in Brochet, X. et al., Nucl. Acids Res. 36, W503-508(2008); Giudicelli, V., Brochet, X., Lefranc, M.-P., Cold Spring Harb Protoc. 2011 Jun 1;2011(6); and in IMGT booklet with generous provision from Cold Spring Harbor (CSH) Protocols.

Amino acid sequences of heavy chain CDR1 to 3 and light chain CDR1 to 3 were specified as set forth in SEQ ID NOs:6 to 11, respectively.

3. Measurement of ADCC Activity by Rat NZ-1 Antibody Against Podoplanin-Positive Cell A 10% FBS-RPMI1640 suspension (containing glutamine) of rat splenocytes was prepared, followed by hemolysis of erythrocytes, and was added to a round-bottom 96-well plate such that splenocytes were at a density of $5 \times 10^5$ cells/well or $1 \times 10^6$ cells/well.

As tumor cells, H2052 cells, H226 cells, and MSTO-211H cells of mesothelioma cells were used. Tumor cells were labeled with 0.1 µCi of $Na^{51}CrO_4$, washed twice, and then mixed at a density of $1 \times 10^4$ cells/well with rat splenocytes.

In addition, rat IgG was added at a final concentration of 1 µg/ml to a control group, and rat NZ-1 antibodies were added at a final concentration of 1 µg/ml to an NZ-1 antibody-administered group. In the above experiment, the Effector/Target ratio was 50 or 100, and a final solution volume was 200 µl/well. The experiment was carried out in triplicate. After incubation in a $CO_2$ incubator at 37° C. for 6 hours, 100 µl of the supernatant was recovered and radioactivity was counted in a gamma counter (E value below).

In addition to the control group and the NZ-1 antibody-administered group, the activity in a well in which tumor cells were incubated with a medium alone was measured as spontaneous release, and the activity in a well incubated with 1% SDS was measured as maximum release. Cellular cytotoxicity (%) was calculated according to the following equation.

% Specific lysis (Cytotoxicity)=$(E-S)/(M-S) \times 100$

E: the release in the test sample (cpm in the supernatant from target cells incubated with effector cells and test antibody)

S: the spontaneous release (cpm in the supernatant from target cells incubated with medium alone)

M: the maximum release (cpm released from target cells lysed with 1% sodium dodecyl sulfate)

Figure 1B:
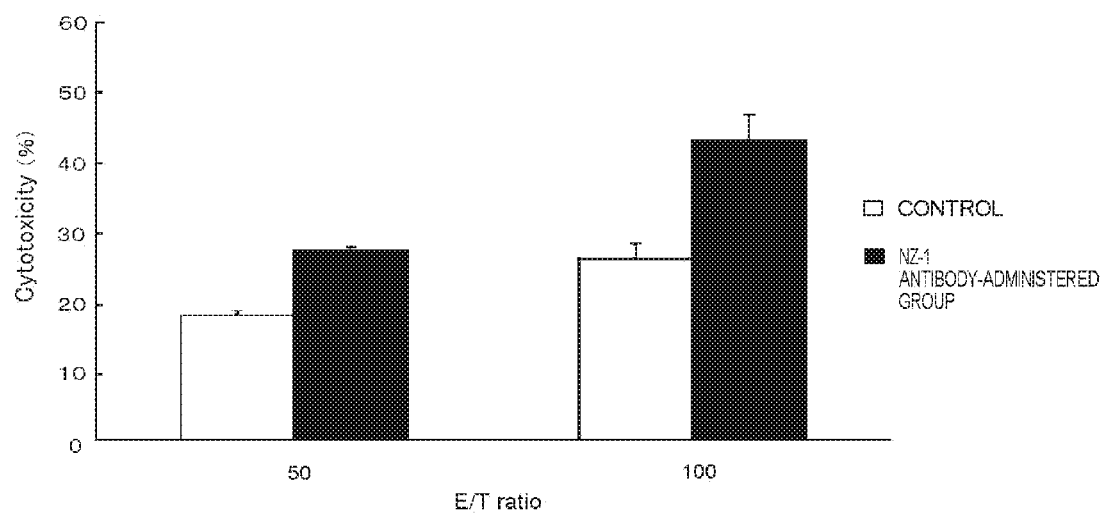
FIG. 1B illustrates the measurement results of ADCC activity of NZ-1 antibody against a mesothelioma cell (H226 cell). ADCC activity by rat NZ-1 antibody was confirmed.
Figure 1C:
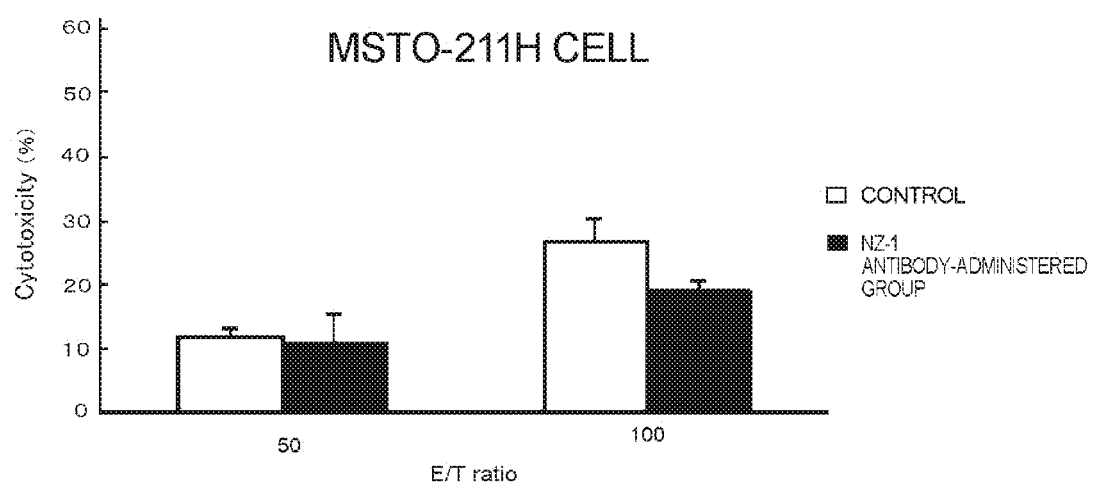
FIG. 1C illustrates the measurement results of ADCC activity of an NZ-1 antibody against a mesothelioma cell (MSTO-211H cell). ADCC activity of rat NZ-1 antibody was not observed.

The results are shown in FIGS. 1A to C.

Meanwhile, the expression of podoplanin in the mesothelioma cells was confirmed by flow cytometry. Specifically, the cells were reacted with NZ-1 antibodies (10 µg/ml) at 4° C. for 30 minutes, and further reacted with anti-rat IgG-FITC antibodies at 4° C. for 30 minutes. Fluorescence intensity was measured by FACSCalibur (BD).

Figure 2A:
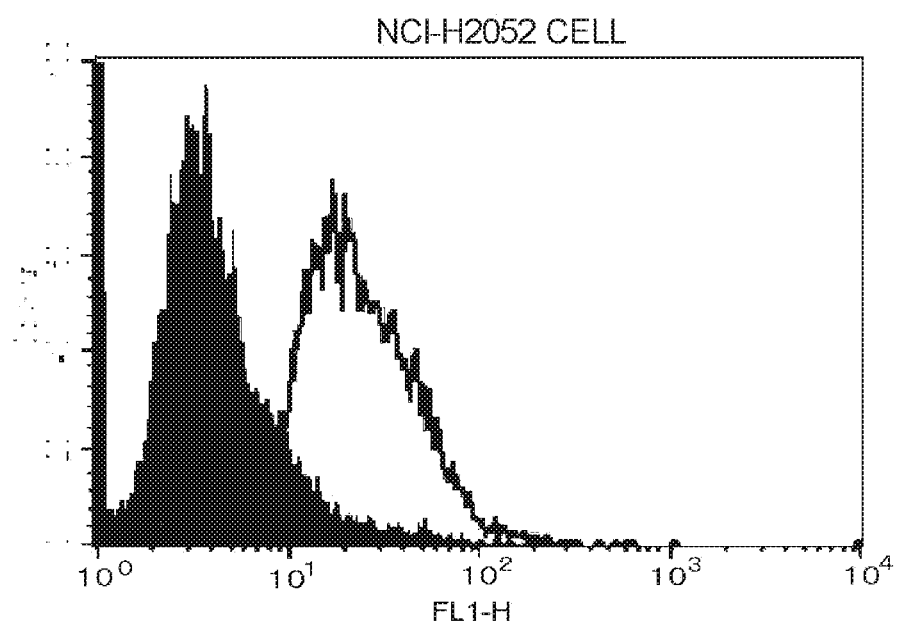
FIG. 2A illustrates the flow cytometry results confirming the expression of podoplanin on mesothelioma cells (H2052 cell). Binding of podoplanin to rat NZ-1 antibody was observed, and the expression of podoplanin was confirmed.
Figure 2B:
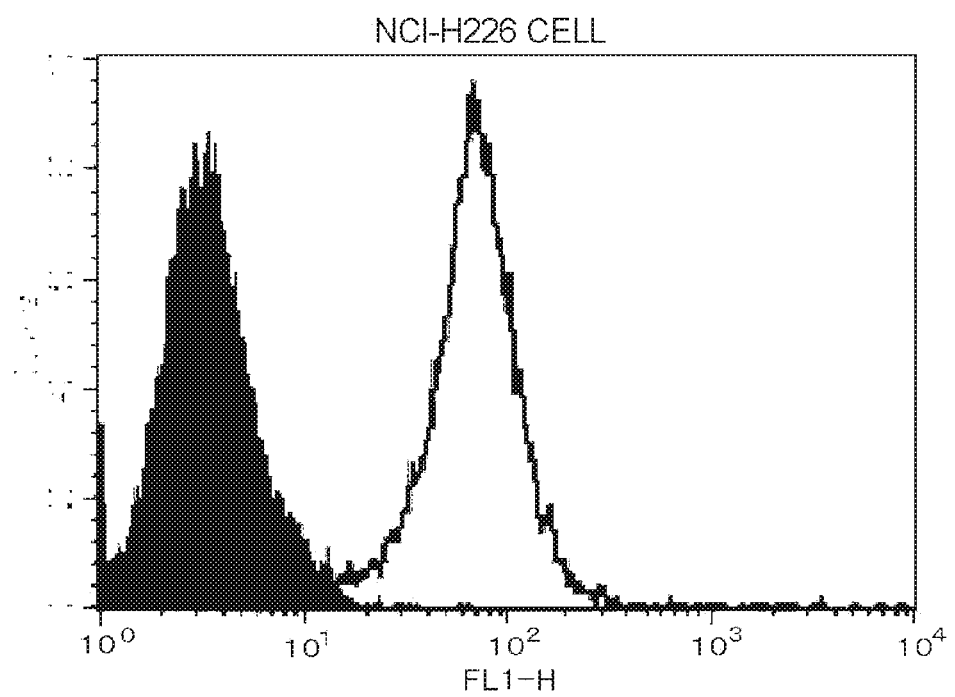
FIG. 2B illustrates the flow cytometry results confirming the expression of podoplanin on mesothelioma cells (H226 cell). Binding of podoplanin to rat NZ-1 antibody was observed, and the expression of podoplanin was confirmed.
Figure 2C:
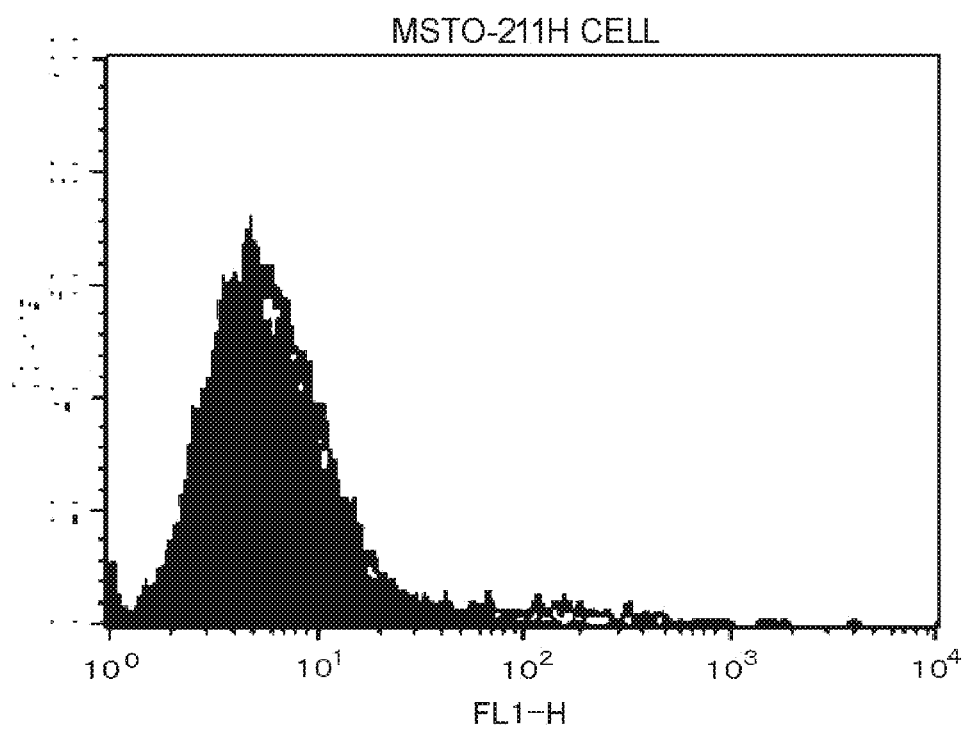
FIG. 2C illustrates the flow cytometry results confirming the expression of podoplanin on mesothelioma cells (MSTO-211H cell). The expression of podoplanin was not observed.

The results are shown in FIGS. 2A to C. A solid line represents NZ-1 antibody, and a solid portion represents a peak of a control with secondary antibody alone.

As shown in FIG. 1 and FIG. 2, ADCC activity by NZ-1 antibodies was confirmed against podoplanin-positive cells. On the other hand, ADCC activity by NZ-1 antibodies was not observed against podoplanin-negative cells.

4. Tumor Growth-Inhibitory Effects by Rat NZ-1 Antibody

Podoplanin-expressing CHO cells (CHO/podoplanin (see Non-Patent Document 3)) were suspended by trypsin treatment, washed with PBS, suspended in HBSS, adjusted to a density of $3.0 \times 10^7$ cells/ml, and subcutaneously implanted into BALB/c nude mice at a dose of 100 µl/animal.

After one day, 200 µl of 5 mg/ml of NZ-1 antibodies and 200 µl of 5 mg/ml of rat IgG were respectively loaded in an Alzet mini-osmotic pump (model 2002, DURECT), implanted into the peritoneal cavity of mice, and the NZ-1 antibody and rat IgG were respectively administered at 0.5 µl (2.5 µg)/hour for two weeks sustainably (control group; n=10, NZ-1 group; n=9). After 20 days from cell implantation, a tumor diameter was measured at intervals of 3 days.

Figure 3:
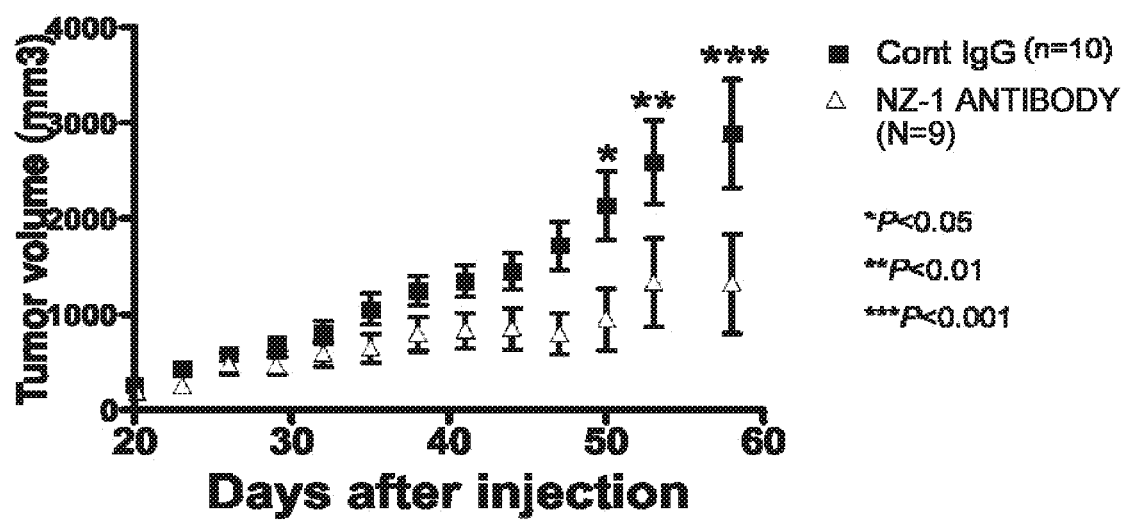
FIG. 3 illustrates the investigation results of tumor growth-inhibitory effects by rat NZ-1 antibody. Administration of rat NZ-1 antibody to a mouse with subcutaneous implantation of CHO/podoplanin exhibited significant inhibition of growth of tumor, as compared to a control group.

The results are shown in FIG. 3. The subcutaneous tumor formation rate was 9/10 (90%) for the control group and 6/9 (66.6%) for the NZ-1 antibody-administered group; the survival rate of implanted tumor was decreased by NZ-1 antibodies. Further, subcutaneous tumors formed were significantly small in the NZ-1 antibody-administered group after 50 days of cell implantation, as compared to the control group. From these results, it was found that the anti-NZ-1 antibody inhibits engraftment and growth of subcutaneous tumor.

5. Detection of Arteriosclerotic Lesion by Rat NZ-1 Antibody 10 mg of tissue of an arteriosclerotic lesion was washed three times with PBS and solubilized with a solubilization solution (1% Triton in PBS; 50 µg/ml aprotinin), and protein quantification was carried out according to common procedure (see Non-Patent Document 3). 10 µl of 2× sample buffer was added to 10 µg (10 µl) of the protein which was then boiled at 100° C. for 5 minutes. 24 µl of the protein solution was applied onto 10% constant gel and subjected to electrophoresis at 40 mA for 55 minutes, using a running buffer (25 mM Tris-HCl (pH 8.3), 192 mM glycine, 0.1% SDS).

Thereafter, the electrophoresed gel was transferred to a PVDF membrane (30V, 60 minutes), and blocked by a blocking buffer (4% skim milk in PBS-0.05% Tween) at 4° C. for 18 hours. Then, the NZ-1 antibodies adjusted to 1 µg/ml by a blocking buffer and 4000-fold diluted anti β-actin antibodies were reacted at room temperature for 50 minutes.

After a wash with a washing buffer (0.05% Tween 20 in PBS), the membrane was reacted with 1000-fold dilution (in a blocking buffer) of HRP-labeled anti-Rat IgG (GE) and HRP-labeled anti-mouse IgG (GE) at room temperature for 45 minutes. After being washed with a washing buffer, color development was carried out by ECL Plus (GE), followed by exposure to a scientific imaging film.

Figure 4:
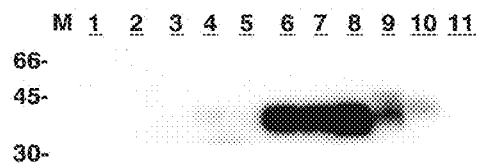
FIG. 4 illustrates the detection results of podoplanin in an arteriosclerotic lesion, using rat NZ-1 antibody. High expression of podoplanin was confirmed in an advanced lesion and a early lesion with macrophage exudation.
Figure 4:
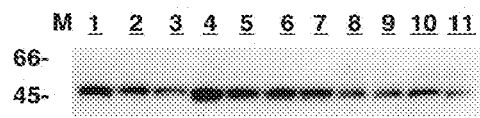

The results are shown in FIG. 4. High expression of podoplanin was confirmed in macrophage-exuding early lesions and advanced lesions.

6. Construction of Mouse Chimera-Type NZ-1 Antibody

For the construction of mouse chimera-type NZ-1 antibody, DNA encoding VH region and CH1 region of NZ-1 was amplified by PCR and introduced into pFUSE-mIgG2A-Fc1 vectors comprising DNA encoding hinge region, CH2 and CH3 regions of mouse IgG2a (pFUSE-mIgG2A/NZ-1H).

The DNA encoding VH region and CH1 region of NZ-1 was amplified by the following primers, using a pcDNA3/NZ-1H plasmids as template.

```
                                        (SEQ ID NO: 29)
EcoRI-NZ-1-Fwd:      cca gaattc tcc tca cca tgg act (SEQ ID NO: 30)
NZ-1-CH1-Rev-BglII:  tgg agatct ccttggcacaattttcttgt
```

As DNA encoding L chain of NZ-1, pcDNA3(G418)/NZ-1L which was constructed upon determination of the base sequence was used.

2 μg of pFUSE-mIgG2A/NZ-1H and 2 μg of pcDNA3 (G418)/NZ-1L (Zeocin) were mixed and transfected into $1 \times 10^5$ of CHO cells (per well of a 6-well plate) according to the method of a Lipofectamin kit. After 24 hours, selection of transfectant cells was carried out with a medium containing 500 μg/ml of Zeocin and 1 mg/ml of G418. For LN319 cells or podoplanin-expressing CHO cells, reactivity of the culture supernatant of the selected cells was confirmed by flow cytometry.

The high-expression strain of chimeric antibodies was incubated using a serum-free medium (Invitrogen), and the culture supernatant was recovered. The culture supernatant was subjected to purification of mouse chimera-type NZ-1 antibodies through a protein G column (Pierce). The mouse chimera-type NZ-1 antibody consists of a heavy chain consisting of the amino acid sequence set forth in SEQ ID NO:23 and a light chain consisting of the amino acid sequence set forth in SEQ ID NO:3. The base sequence of DNA encoding the heavy chain is set forth in SEQ ID NO:24, and the base sequence of DNA encoding the light chain is set forth in SEQ ID NO:5.

Figure 5:
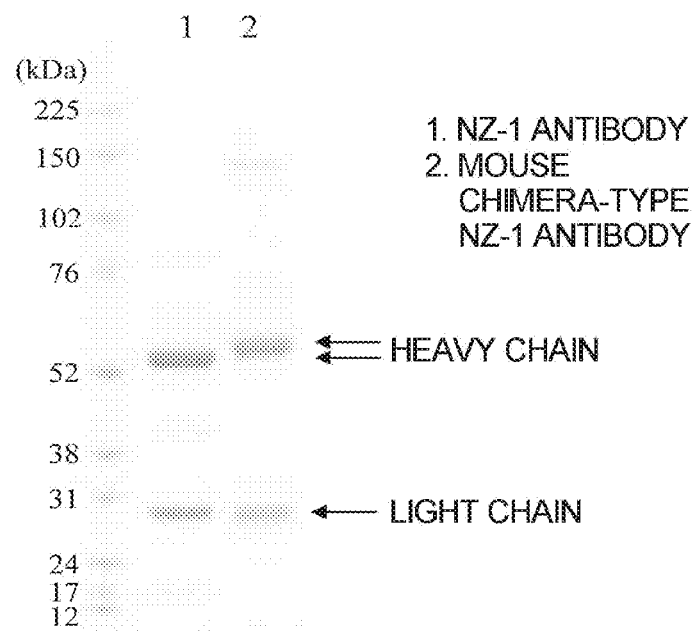
FIG. 5 illustrates SDS-PAGE electrophoresis results of rat NZ-1 antibody and a mouse chimera-type NZ-1 antibody.

2 μg of the purified NZ-1 antibodies and 2 μg of the purified mouse chimera-type NZ-1 antibodies were subjected to SDS-PAGE electrophoresis, followed by CBB staining. The results are shown in FIG. 5.

7. Construction of Human Chimera-Type NZ-1 Antibody

For the construction of human chimera-type NZ-1 antibodies, DNA encoding VH region of NZ-1 was amplified by PCR and introduced into pcDNA3.3 vectors comprising DNA encoding CH1, hinge region, CH2, and CH3 regions of human IgG1 (pcDNA3.3-hIgG1/NZ-1H). VH region of NZ-1 was amplified by the following primers, using pcDNA3/NZ-1H plasmids as template.

```
                                (SEQ ID NO: 31)
NZ-1 VH-F primer:    TCCTCACCATGGACTTCAGG (SEQ ID NO: 32)
NZ-1 VH-R primer:    TTCAGCTGAGGAGACTGTGA
```

With regard to L chain of NZ-1, DNA encoding VL region of NZ-1 was amplified by PCR and introduced into pcDNA3.1 vectors comprising DNA encoding CL region of κ chain of human IgG (pcDNA3.1-hIgCL/NZ-1L). The DNA encoding VL region of NZ-1 was amplified by the following primers, using pcDNA3/NZ-1L plasmids as template.

```
                                (SEQ ID NO: 33)
NZ-1VL-F primer:     accATGACATGGACTCTACT (SEQ ID NO: 34)
NZ-1VL-R primer:     CTTGGGCTGACCTAGGACA
```

2 μg of each of pcDNA3.3-hIgG1/NZ-1H(G418)/pcDNA3.1-hIgCL/NZ-1L (Zeocin) was mixed and transfected into $1 \times 10^5$ of CHO cells (per well of a 6-well plate) according to the method of a Lipofectamin kit. After 24 hours, selection of transfectant cells was carried out with a medium containing 500 μg/ml of Zeocin and 1 mg/ml of G418. For H226 cells, LN319 cells or podoplanin-expressing CHO cells, reactivity of the culture supernatant of the selected cells was confirmed by flow cytometry.

The high-expression strain of a human chimera-type antibody was incubated using a serum-free medium (Invitrogen), and the culture supernatant was recovered. The culture supernatant was subjected to purification of a human chimera-type NZ-1 antibody through a protein G column (Pierce). The human chimera-type NZ-1 antibody consists of a heavy chain including the amino acid sequence set forth in SEQ ID NO:37 and a light chain including the amino acid sequence set forth in SEQ ID NO:39. The base sequence of DNA encoding a heavy chain is set forth in SEQ ID NO:38, and the base sequence of DNA encoding an light chain is set forth in SEQ ID NO:40. The heavy chain consists of VH region of rat NZ-1 antibody and CH1, hinge region, CH2, CH3 derived from human IgG1. The light chain consists of VL region of rat NZ-1 antibody and CL derived from human IgG1.

Figure 6:
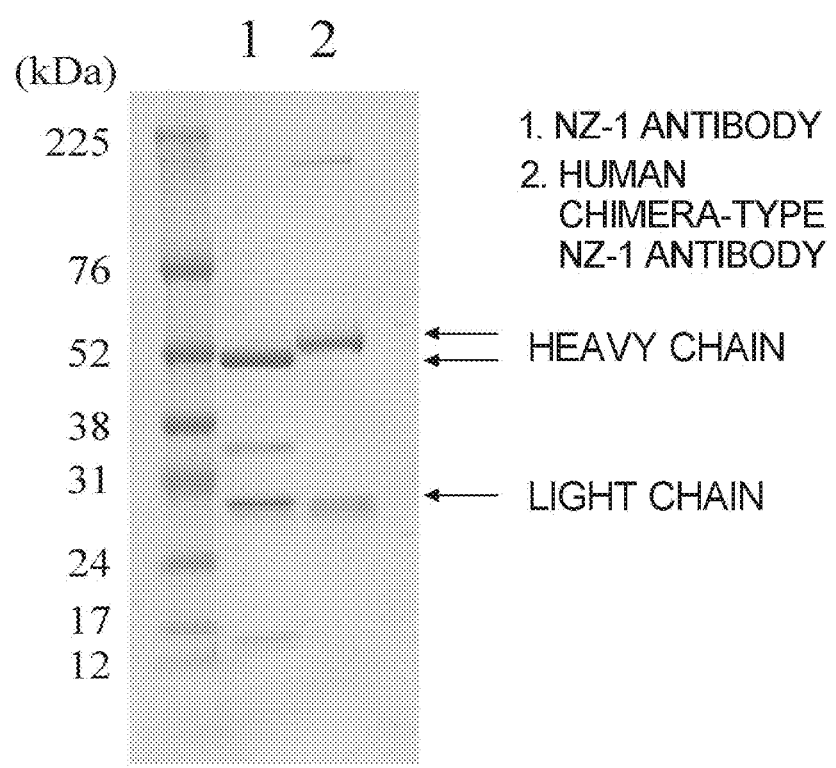
FIG. 6 illustrates the SDS-PAGE electrophoresis results of rat NZ-1 antibody and a human chimera-type NZ-1 antibody.

2 μg of the purified NZ-1 antibody and 2 μg of the human chimera-type NZ-1 antibody were subjected to SDS-PAGE electrophoresis, followed by CBB staining. The results are shown in FIG. 6.

8. Reactivity of NZ-1 Antibody, Mouse Chimera-Type NZ-1 Antibody, and Human Chimera-Type Nz-1 Antibody with Podoplanin The human chimera-type NZ-1 antibody was confirmed as exhibiting reactivity with podoplanin. First, NZ-1 antibodies, mouse chimera-type NZ-1 antibodies, and human chimera-type NZ-1 antibodies (10 μg/ml) were reacted at 4° C. for 30 minutes with human malignant mesothelioma cells (H226) and human glioma cells (LN319) which expressed human podoplanin. In addition, anti-rat IgG-FITC antibodies, anti-mouse IgG-FITC antibodies, and anti-human IgG-FITC antibodies were respectively reacted at 4° C. for 30 minutes. The fluorescence intensity was measured by FACSCalibur (BD).

Figure 7:
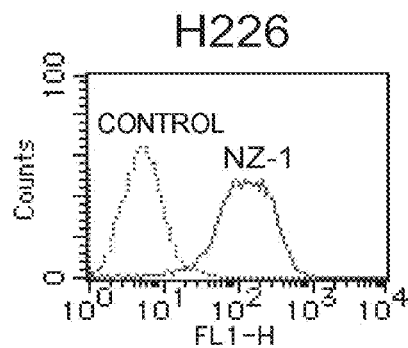
FIG. 7 illustrates the flow cytometry results showing the reactivity of rat NZ-1 antibody, mouse chimera-type NZ-1 antibody, and human chimera-type NZ-1 antibody to podoplanin. It was confirmed that all antibodies react well with human glioma cells LN319 or mesothelioma cells H226, which express human podoplanin.
Figure 7:
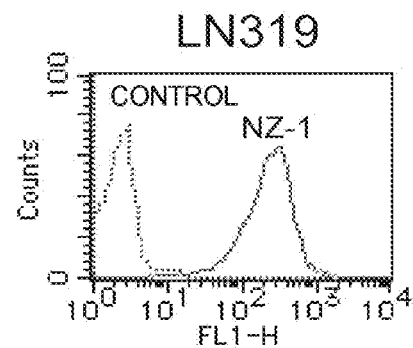
Figure 7:
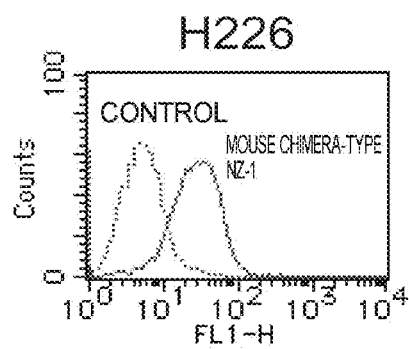
Figure 7:
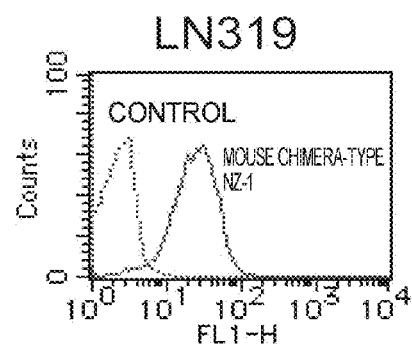
Figure 7:
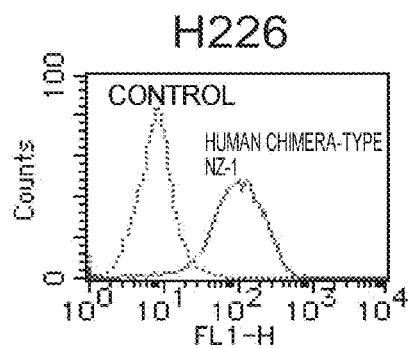
Figure 7:
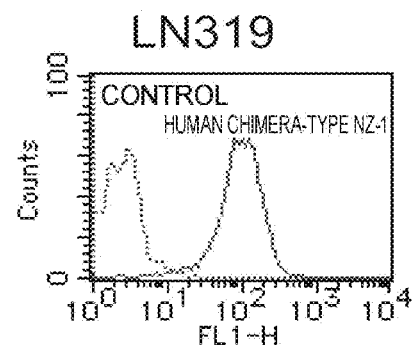

The results are shown in FIG. 7. As shown in FIG. 7, all of the NZ-1 antibodies, the mouse chimera-type NZ-1 antibodies, and the human chimera-type NZ-1 antibodies reacted well with the human malignant mesothelioma cells (H226) and the human glioma cells (LN319) which expressed human podoplanin. As a negative control, secondary antibodies of each were used alone.

9. Measurement of CDC Activity of Rat NZ-1 Antibody and Mouse Chimera-Type NZ-1 Antibody (after 6 Hours and 24 Hours of Incubation)

Tumor cells (H226 cell) were labeled with 0.1 µCi of $Na^{51}CrO_4$, washed twice, and then added at a density of $1\times10^4$ cells/well to a round-bottom 96-well plate. Rat NZ-1 antibodies or mouse chimera-type NZ-1 (normal rat antibodies and normal mouse antibodies are a control antibodies of each) were added to a final concentration of 1 µg/ml, and a rabbit complement was added to achieve 4-fold dilution.

The final solution volume was set to 200 µl/well. After incubation in a $CO_2$ incubator at 37° C. for 6 hours or 24 hours, 100 µl of the supernatant was recovered, and radioactivity was counted in a gamma counter. In addition to the control group, the NZ-1 antibody-administered group and the mouse chimera-type NZ-1 antibody-administered group, the activity in a well in which tumor cells were incubated with a medium alone was measured as spontaneous release, and the activity in a well incubated with 1% SDS was measured as maximum release. Cellular cytotoxicity (%) was calculated according to the following equation.

$$\% \text{ Specific lysis (Cytotoxicity)}=(E-S)/(M-S)\times100$$

E: the release in the test sample (cpm in the supernatant from target cells incubated with effector cells and test antibody)

S: the spontaneous release (cpm in the supernatant from target cells incubated with medium alone)

M: the maximum release (cpm released from target cells lysed with 1% sodium dodecyl sulfate)

Figure 8A:
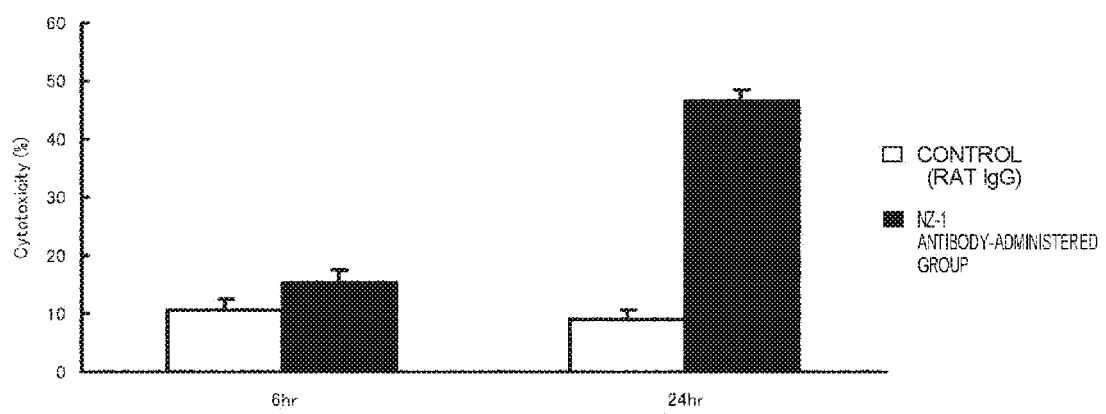
FIG. 8A illustrates the measurement results of CDC activity by rat NZ-1 antibody against H226 cells. It was confirmed that rat NZ-1 antibody has CDC activity.
Figure 8B:
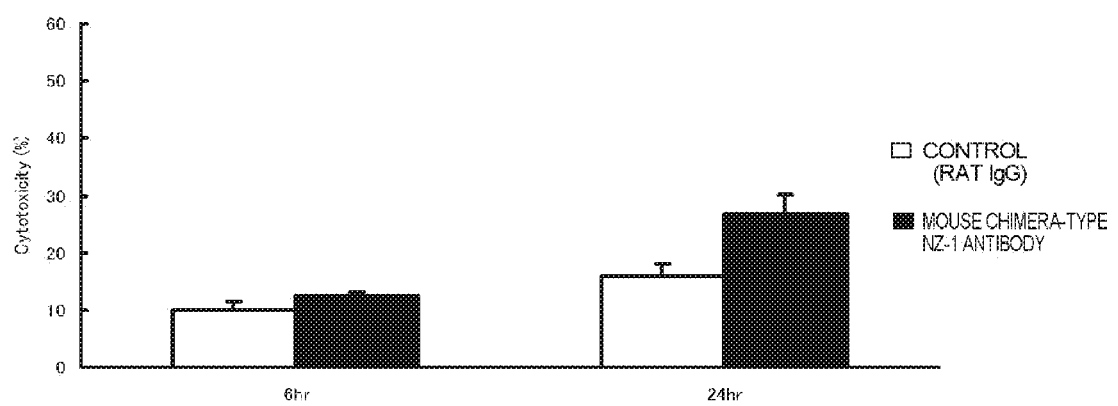
FIG. 8B illustrates the measurement results of CDC activity by a mouse chimera-type NZ-1 antibody against H226 cells. It was confirmed that a mouse chimera-type NZ-1 antibody also has CDC activity.

The results are shown in FIGS. 8A and B.

After incubation for 6 hours, it was found that both of rat NZ-1 antibodies and mouse chimera-type NZ-1 antibodies have CDC activity against podoplanin-positive human tumor cells. After incubation for 24 hours, CDC activity was also increased. The increase rate of cellular cytotoxicity relative to the control group was slightly low in a mouse chimera-type NZ-1 antibody, as compared to rat NZ-1 antibody.

10. Measurement of ADCC Activity of Rat NZ-1 Antibody, Mouse Chimera-Type NZ-1 Antibody and Human Chimera-Type NZ-1 Antibody A suspension of peripheral blood mononuclear cells (MNCs) of a healthy subject isolated by a specific gravity centrifugation method was prepared, and MNCs were added at a density of $1\times10^6$ cells/well to a round-bottom 96-well plate. Human malignant mesothelioma cells (H226) and human glioma cells (LN319) were labeled with 0.1 µCi of $Na^{51}CrO_4$, washed twice, and then mixed at a density of $1\times10^4$ cells/well with MNCs. In addition, rat IgG and human IgG as controls, NZ-1, mouse chimera-type antibodies, and human chimera-type antibodies were each added to a final concentration of 1 µg/ml. In the above experiment, the Effector/Target ratio was 100, and a final solution volume was 200 µl/well. The experiment was carried out in triplicate. After incubation in a $CO_2$ incubator at 37° C. for 6 hours, 100 µl of the supernatant was recovered and radioactivity was counted in a gamma counter. The activity in a well in which the labeled tumor cells were incubated with a medium alone was measured as spontaneous release, and the activity in a well incubated with 1% SDS was measured as maximum release. Cellular cytotoxicity (%) was calculated according to the following equation.

$$\% \text{ Specific lysis}=(E-S)/(M-S)\times100$$

E: the release in the test sample (cpm in the supernatant from target cells incubated with effector cells and test antibody)

S: the spontaneous release (cpm in the supernatant from target cells incubated with medium alone)

M: the maximum release (cpm released from target cells lysed with 1% sodium dodecyl sulfate)

Figure 9:
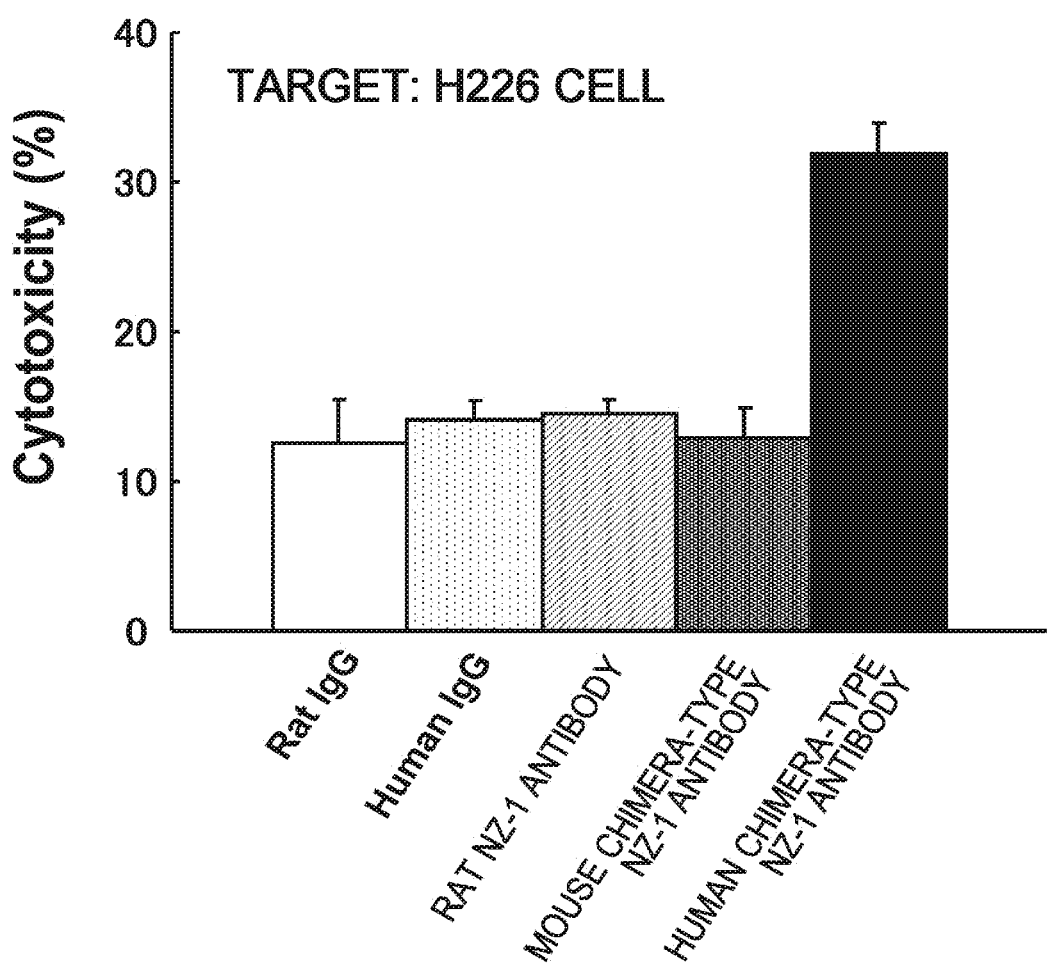
FIG. 9 illustrates the measurement results of ADCC activity by rat NZ-1 antibody, a mouse chimera-type NZ-1 antibody, and a human chimera-type NZ-1 antibody against H226 cells. A human chimera-type NZ-1 antibody exhibited a remarkably high ADCC activity, as compared to rat NZ-1 antibody and a mouse chimera-type NZ-1 antibody.
Figure 10:
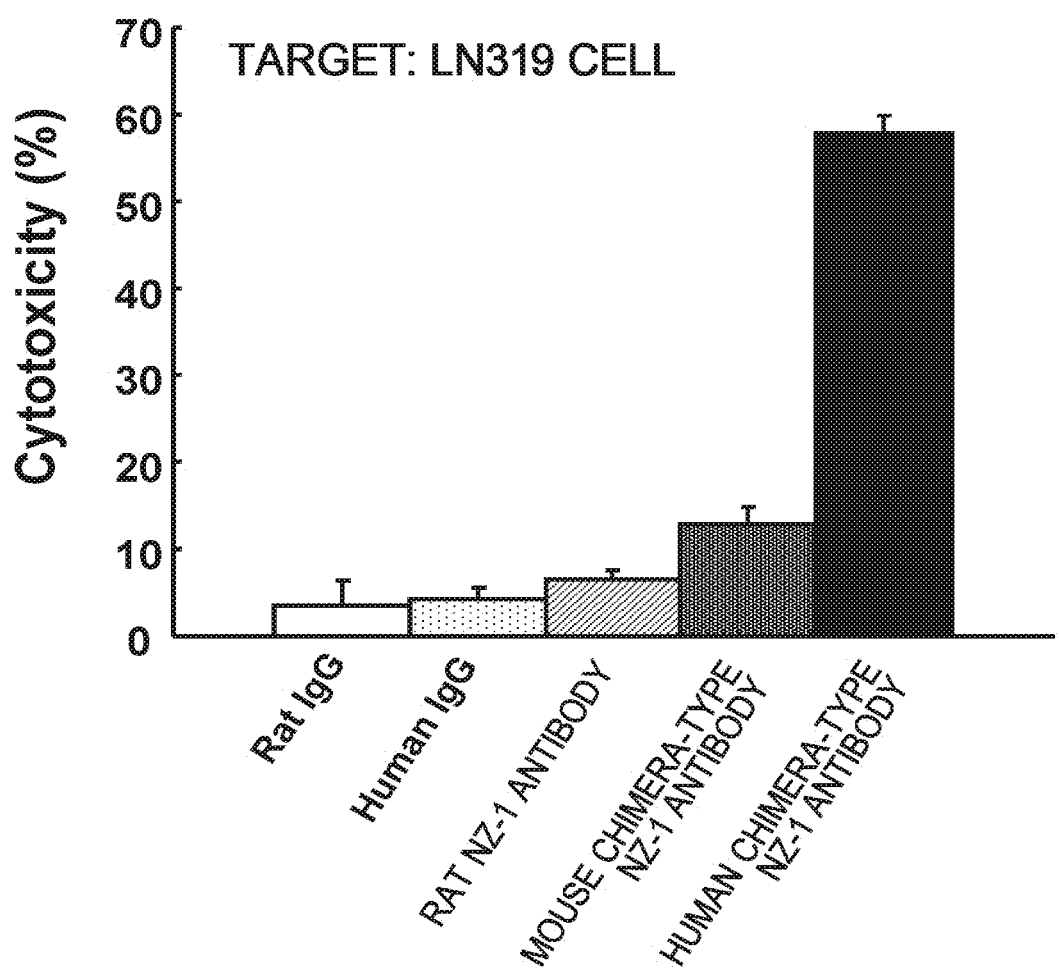
FIG. 10 illustrates the measurement results of ADCC activity by rat NZ-1 antibody, mouse chimera-type NZ-1 antibody, and human chimera-type NZ-1 antibody against LN319 cells. A human chimera-type NZ-1 antibody exhibited a remarkably high ADCC activity, as compared to rat NZ-1 antibody and a mouse chimera-type NZ-1 antibody.

The results are shown in FIGS. 9 and 10.

Where human effector cells were employed, mouse chimera-type NZ-1 antibodies and human chimera-type NZ-1 antibodies were found to have ADCC activity against podoplanin-positive human tumor cells. In particular, the human chimera-type NZ-1 antibody was confirmed to exhibit a remarkably high ADCC activity, as compared to the rat NZ-1 antibody and the mouse chimera-type NZ-1 antibody. Since the mouse chimera-type NZ-1 antibody was merely confirmed to have ADCC activity equal to that of the NZ-1 antibody, such a remarkable rise of the activity of the human chimera-type NZ-1 antibody was beyond expectation by those skilled in the art.

11. Measurement of CDC activity of rat NZ-1 antibody, Mouse Chimera-Type NZ-1 Antibody and Human Chimera-Type NZ-1 Antibody Human malignant mesothelioma cells (H226) and Human glioma cells (LN319) were labeled with 0.1 µCi of $Na^{51}CrO_4$, washed twice, and then added at a density of $1\times10^4$ cells/well to a round-bottom 96-well plate. Rat IgG and human IgG as controls, NZ-1, mouse chimera-type NZ-1 antibodies, and human chimera-type NZ-1 antibodies were each added to a final concentration of 1 µg/ml, and a rabbit complement was finally added thereto to achieve 4-fold dilution. The final solution volume was set to 200 µl/well. After incubation in a $CO_2$ incubator at 37° C. for 6 hours, 100 µl of the supernatant was recovered, and radioactivity was counted in a gamma counter. The activity in a well in which tumor cells were incubated with a medium alone was measured as spontaneous release, and the activity in a well incubated with 1% SDS was measured as maximum release. Cellular cytotoxicity (%) was calculated according to the following equation.

$$\% \text{ Specific lysis}=(E-S)/(M-S)\times100$$

E: the release in the test sample (cpm in the supernatant from target cells incubated with effector cells and test antibody)

S: the spontaneous release (cpm in the supernatant from target cells incubated with medium alone)

M: the maximum release (cpm released from target cells lysed with 1% sodium dodecyl sulfate)

Figure 11:
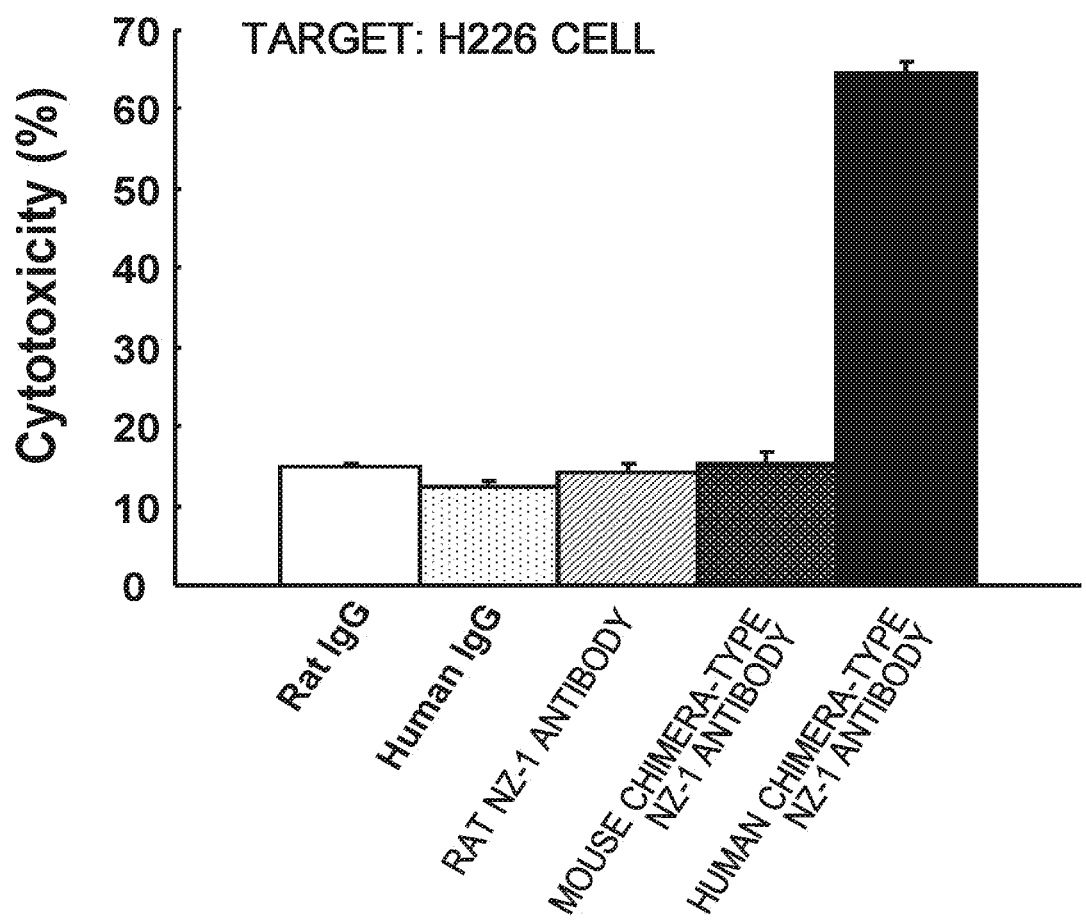
FIG. 11 illustrates the measurement results of CDC activity by rat NZ-1 antibody, mouse chimera-type NZ-1 antibody, and human chimera-type NZ-1 antibody against H226 cells. A human chimera-type NZ-1 antibody exhibited a remarkably high CDC activity, as compared to rat NZ-1 antibody and a mouse chimera-type NZ-1 antibody.
Figure 12:
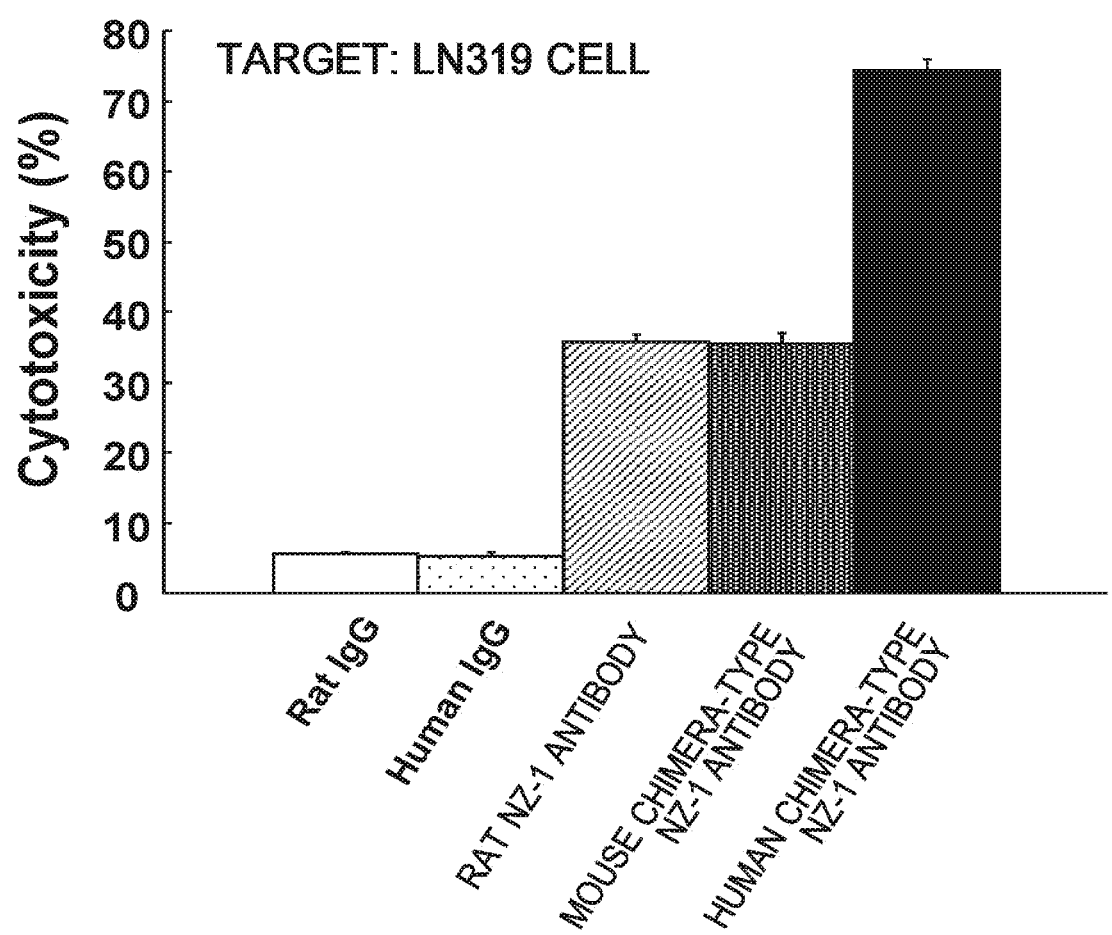
FIG. 12 illustrates the measurement results of CDC activity by rat NZ-1 antibody, mouse chimera-type NZ-1 antibody, and human chimera-type NZ-1 antibody against LN319 cells. A human chimera-type NZ-1 antibody exhibited a remarkably high CDC activity, as compared to rat NZ-1 antibody and a mouse chimera-type NZ-1 antibody.
Figure 13:
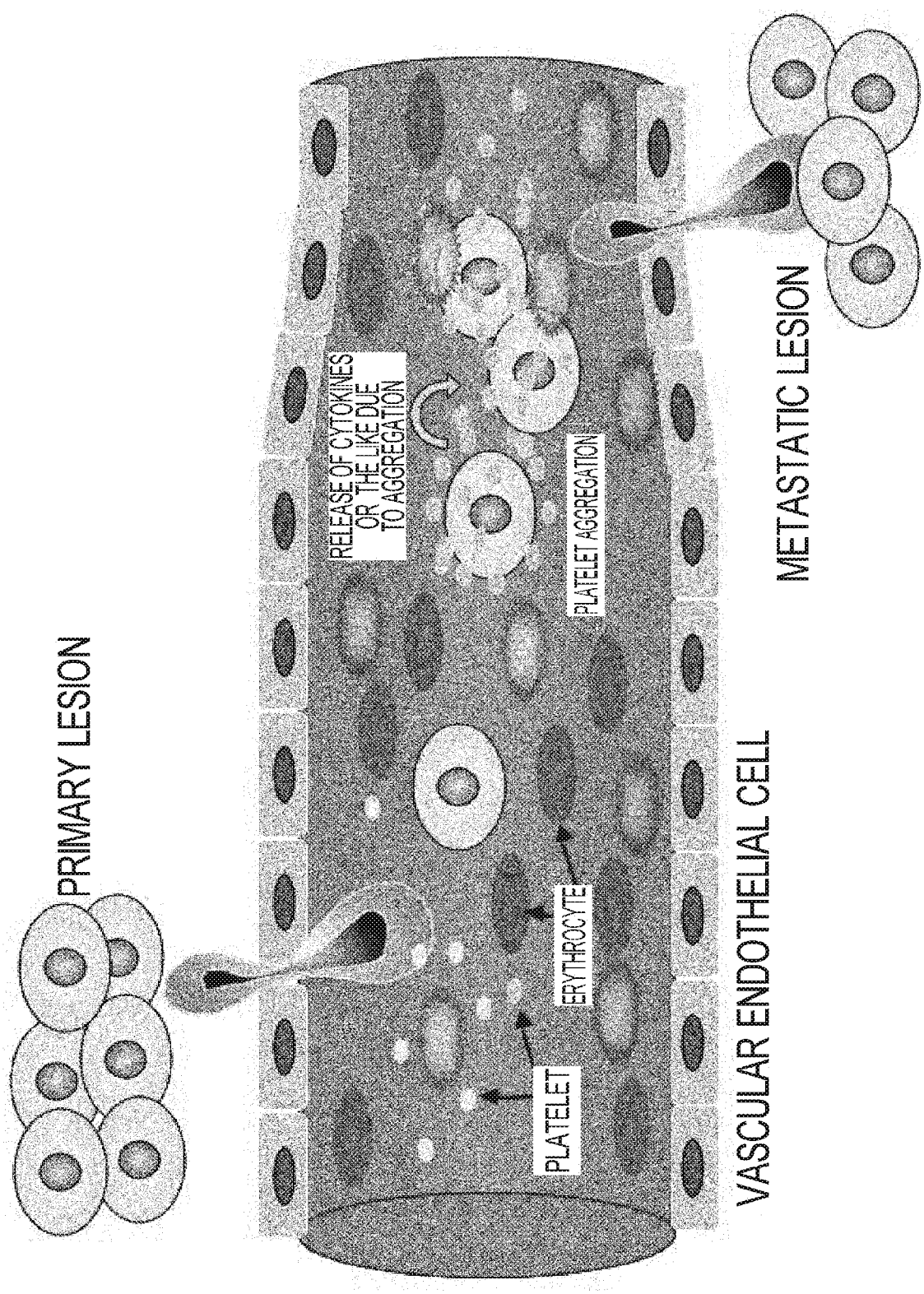
FIG. 13 is a conceptual diagram showing the relationship between platelet aggregation and cancer metastasis.

The results are shown in FIG. 11 and FIG. 12.

All of the rat NZ-1 antibody, the mouse chimera-type NZ-1 antibody, and the human chimera-type antibody were found to have a CDC activity against podoplanin-positive human tumor cells. In particular, the human chimera-type NZ-1 antibody was confirmed to exhibit a remarkably high CDC activity, as compared to the rat NZ-1 antibody and the mouse chimera-type NZ-1 antibody. Since the mouse chimera-type NZ-1 antibody was merely confirmed to have cellular cytotoxicity equal to that of the NZ-1 antibody, such a remarkable rise of the activity by a human chimera-type antibody was beyond expectation by those skilled in the art.

[Sequence List in Free Text]

SEQ ID NO:1 is the epitope of rat NZ-1 antibody.
SEQ ID NO:2 is the amino acid sequence of rat NZ-1 antibody H chain.
SEQ ID NO:3 is the amino acid sequence of rat NZ-1 antibody L chain.
SEQ ID NO:4 is the base sequence of DNA encoding rat NZ-1 antibody H chain.
SEQ ID NO:5 is the base sequence of DNA encoding rat NZ-1 antibody L chain.

SEQ ID NO:6 is the amino acid sequence of rat NZ-1 antibody H chain CDR1.
SEQ ID NO:7 is the amino acid sequence of rat NZ-1 antibody H chain CDR2.
SEQ ID NO:8 is the amino acid sequence of rat NZ-1 antibody H chain CDR3.
SEQ ID NO:9 is the amino acid sequence of rat NZ-1 antibody L chain CDR1.
SEQ ID NO:10 is the amino acid sequence of rat NZ-1 antibody L chain CDR2.
SEQ ID NO:11 is the amino acid sequence of rat NZ-1 antibody L chain CDR3.
SEQ ID NO:12 is the base sequence of DNA encoding rat NZ-1 antibody H chain CDR1.
SEQ ID NO:13 is the base sequence of DNA encoding rat NZ-1 antibody H chain CDR2.
SEQ ID NO:14 is the base sequence of DNA encoding rat NZ-1 antibody H chain CDR3.
SEQ ID NO:15 is the base sequence of DNA encoding rat NZ-1 antibody L chain CDR1.
SEQ ID NO:16 is the base sequence of DNA encoding rat NZ-1 antibody L chain CDR2.
SEQ ID NO:17 is the base sequence of DNA encoding rat NZ-1 antibody L chain CDR3.
SEQ ID NO:18 is the amino acid sequence of rat NZ-1 antibody H chain variable region (VH).
SEQ ID NO:19 is the amino acid sequence of rat NZ-1 antibody L chain variable region (VL).
SEQ ID NO:20 is the amino acid sequence of rat NZ-1 antibody H chain constant region 1 (CH1).
SEQ ID NO:21 is the amino acid sequence of rat NZ-1 antibody L chain constant region (CL).
SEQ ID NO:22 is the amino acid sequence of an Fc region of a mouse antibody.
SEQ ID NO:23 is the amino acid sequence of a mouse chimera-type NZ-1 antibody H chain.
SEQ ID NO:24 is the base sequence of DNA encoding a mouse chimera-type NZ-1 antibody H chain.
SEQ ID NO:25 is the primer for amplification of rat NZ-1 antibody H chain.
SEQ ID NO:26 is the primer for amplification of rat NZ-1 antibody H chain.
SEQ ID NO:27 is the primer for amplification of rat NZ-1 antibody L chain.
SEQ ID NO:28 is the primer for amplification of rat NZ-1 antibody L chain.
SEQ ID NO:29 is the primer for amplification of rat NZ-1 antibody VH/CH1.
SEQ ID NO:30 is the primer for amplification of rat NZ-1 antibody VH/CH1.
SEQ ID NO:31 is the primer for amplification of a VH region of rat NZ-1 antibody.
SEQ ID NO:32 is the primer for amplification of a VH region of rat NZ-1 antibody.
SEQ ID NO:33 is the primer for amplification of a VL region of rat NZ-1 antibody.
SEQ ID NO:34 is the primer for amplification of a VL region of rat NZ-1 antibody.
SEQ ID NO:35 is the amino acid sequence of CH1, hinge region, CH2 and CH3 of a human IgG1.
SEQ ID NO:36 is the amino acid sequence of CL of a human IgG1.
SEQ ID NO:37 is the amino acid sequence of an H chain of a human chimera-type NZ-1 antibody.
SEQ ID NO:38 is the base sequence of DNA encoding an H chain of a human chimera-type NZ-1 antibody.
SEQ ID NO:39 is the amino acid sequence of an L chain of a human chimera-type NZ-1 antibody.
SEQ ID NO:40 is the base sequence of DNA encoding an L chain of a human chimera-type NZ-1 antibody.

The invention claimed is:

1. A human chimeric anti-podoplanin antibody for which an epitope is a polypeptide consisting of the amino acid sequence set forth in SEQ ID NO:1, comprising the following polypeptides:
   a) a heavy chain CDR1 consisting of the amino acid sequence set forth in SEQ ID NO:6;
   b) a heavy chain CDR2 consisting of the amino acid sequence set forth in SEQ ID NO:7;
   c) a heavy chain CDR3 consisting of the amino acid sequence set forth in SEQ ID NO:8;
   d) a light chain CDR1 consisting of the amino acid sequence set forth in SEQ ID NO:9;
   e) a light chain CDR1 consisting of the amino acid sequence set forth in SEQ ID NO:10;
   f) a light chain CDR1 consisting of the amino acid sequence set forth in SEQ ID NO:11.

2. The antibody according to claim 1, comprising VH and VL regions of rat NZ-1 antibody consisting of the amino acid sequence set forth in SEQ ID NO: 18 and 19, respectively, and the CH1, CL, hinge region, CH2, and CH3 of a human antibody.

3. The antibody according to claim 1, comprising a human IgG1 subclass.

4. A chimeric anti-podoplanin antibody comprising the aminco acid sequence set forth in SEQ ID NO:23.

5. A chimeric anti-podoplanin antibody comprising the aminco acid sequence set forth in SEQ ID NO:37.

6. A chimeric anti-podoplanin antibody comprising the aminco acid sequence set forth in SEQ ID NO:39.

* * * * *

```
                         SEQUENCE LISTING

<160> NUMBER OF SEQ ID NOS: 40

<210> SEQ ID NO 1
<211> LENGTH: 6
<212> TYPE: PRT
<213> ORGANISM: Rattus norvegicus
<220> FEATURE:
<223> OTHER INFORMATION: epitope of NZ-1 antibody

<400> SEQUENCE: 1

Ala Met Pro Gly Ala Glu
1               5

<210> SEQ ID NO 2
<211> LENGTH: 458
<212> TYPE: PRT
<213> ORGANISM: Rattus norvegicus
<220> FEATURE:
<223> OTHER INFORMATION: heavy chain of NZ-1 antibody

<400> SEQUENCE: 2

Met Asp Phe Arg Leu Ser Leu Ala Phe Leu Val Leu Leu Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45
```

Ser Asn Tyr Gly Met Ala Trp Val Arg Gln Thr Pro Thr Lys Gly Leu
 50                  55                  60

Glu Trp Ile Ala Ser Ile Ser Ala Gly Gly Asp Lys Thr Tyr Tyr Gly
65                  70                  75                  80

Asp Ser Val Lys Gly Arg Phe Ser Ile Ser Arg Asp Asn Ala Lys Thr
                 85                  90                  95

Thr His Tyr Leu Gln Met Asp Ser Leu Arg Ser Glu Asp Thr Ala Thr
                100                 105                 110

Tyr Tyr Cys Ala Lys Thr Ser Arg Val Tyr Phe Asp Tyr Trp Gly Gln
            115                 120                 125

Gly Val Met Val Thr Val Ser Ser Ala Glu Thr Thr Ala Pro Ser Val
130                 135                 140

Tyr Pro Leu Ala Pro Gly Thr Ala Leu Lys Ser Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ala Leu Ser Ser Gly Val His Thr Phe Pro Ala Val
                180                 185                 190

Leu Gln Ser Gly Leu Tyr Thr Leu Thr Ser Ser Val Thr Val Pro Ser
            195                 200                 205

Ser Thr Trp Ser Ser Gln Ala Val Thr Cys Asn Val Ala His Pro Ala
210                 215                 220

Ser Ser Thr Lys Val Asp Lys Lys Ile Val Pro Arg Glu Cys Asn Pro
225                 230                 235                 240

Cys Gly Cys Thr Gly Ser Glu Val Ser Ser Val Phe Ile Phe Pro Pro
                245                 250                 255

Lys Thr Lys Asp Val Leu Thr Ile Thr Leu Thr Pro Lys Val Thr Cys
                260                 265                 270

Val Val Val Asp Ile Ser Gln Asn Asp Pro Glu Val Arg Phe Ser Trp
            275                 280                 285

Phe Ile Asp Asp Val Glu Val His Thr Ala Gln Thr His Ala Pro Glu
290                 295                 300

Lys Gln Ser Asn Ser Thr Leu Arg Ser Val Ser Glu Leu Pro Ile Val
305                 310                 315                 320

His Arg Asp Trp Leu Asn Gly Lys Thr Phe Lys Cys Lys Val Asn Ser
                325                 330                 335

Gly Ala Phe Pro Ala Pro Ile Glu Lys Ser Ile Ser Lys Pro Glu Gly
                340                 345                 350

Thr Pro Arg Gly Pro Gln Val Tyr Thr Met Ala Pro Pro Lys Glu Glu
            355                 360                 365

Met Thr Gln Ser Gln Val Ser Ile Thr Cys Met Val Lys Gly Phe Tyr
370                 375                 380

Pro Pro Asp Ile Tyr Thr Glu Trp Lys Met Asn Gly Gln Pro Gln Glu
385                 390                 395                 400

Asn Tyr Lys Asn Thr Pro Pro Thr Met Asp Thr Asp Gly Ser Tyr Phe
                405                 410                 415

Leu Tyr Ser Lys Leu Asn Val Lys Lys Glu Thr Trp Gln Gln Gly Asn
            420                 425                 430

Thr Phe Thr Cys Ser Val Leu His Glu Gly Leu His Asn His His Thr
            435                 440                 445

Glu Lys Ser Leu Ser His Ser Pro Gly Lys
450                 455

```
<210> SEQ ID NO 3
<211> LENGTH: 233
<212> TYPE: PRT
<213> ORGANISM: Rattus norvegicus
<220> FEATURE:
<223> OTHER INFORMATION: light chain of NZ-1 antibody

<400> SEQUENCE: 3

Met Thr Trp Thr Leu Leu Phe Leu Ala Phe Leu His His Leu Thr Gly
1               5                   10                  15

Ser Cys Ala Gln Phe Val Leu Thr Gln Pro Asn Ser Val Ser Thr Asn
            20                  25                  30

Leu Gly Ser Thr Val Lys Leu Ser Cys Lys Arg Ser Thr Gly Asn Ile
        35                  40                  45

Gly Ser Asn Tyr Val Asn Trp Tyr Gln Gln His Glu Gly Arg Ser Pro
    50                  55                  60

Thr Thr Met Ile Tyr Arg Asp Asp Lys Arg Pro Asp Gly Val Pro Asp
65                  70                  75                  80

Arg Phe Ser Gly Ser Ile Asp Arg Ser Ser Asn Ser Ala Leu Leu Thr
                85                  90                  95

Ile Asn Asn Val Gln Thr Glu Asp Glu Ala Asp Tyr Phe Cys His Ser
            100                 105                 110

Tyr Ser Ser Gly Ile Val Phe Gly Gly Gly Thr Lys Leu Thr Val Leu
        115                 120                 125

Gly Gln Pro Lys Ser Thr Pro Thr Leu Thr Val Phe Pro Pro Ser Thr
130                 135                 140

Glu Glu Leu Gln Gly Asn Lys Ala Thr Leu Val Cys Leu Ile Ser Asp
145                 150                 155                 160

Phe Tyr Pro Ser Asp Val Glu Val Ala Trp Lys Ala Asn Gly Ala Pro
                165                 170                 175

Ile Ser Gln Gly Val Asp Thr Ala Asn Pro Thr Lys Gln Gly Asn Lys
            180                 185                 190

Tyr Ile Ala Ser Ser Phe Leu Arg Leu Thr Ala Glu Gln Trp Arg Ser
        195                 200                 205

Arg Asn Ser Phe Thr Cys Gln Val Thr His Glu Gly Asn Thr Val Glu
210                 215                 220

Lys Ser Leu Ser Pro Ala Glu Cys Val
225                 230

<210> SEQ ID NO 4
<211> LENGTH: 1377
<212> TYPE: DNA
<213> ORGANISM: Rattus norvegicus
<220> FEATURE:
<223> OTHER INFORMATION: DNA coding for heavy chain of NZ-1 antibody

<400> SEQUENCE: 4
atggacttca ggctcagctt ggctttcctt gtccttttaa taaaaggtgt ccagtgtgag        60
gtgcagctgg tggagtctgg gggaggctta gtgcagcctg aaggtccct gaaactctcc      120 tgtgcagcct caggattcac tttcagtaac tatggcatgg cctgggtccg ccagactcca      180
acgaagggtc tggagtggat cgcatccatt agtgctggtg gtgataaaac ttactatgga      240
gactccgtga aggccgatt cagtatctcc agagataatg caaaaccac ccactacttg       300 caaatggaca gtctgaggtc tgaggacacg gccacttatt actgtgcaaa aacttcccgg      360
gtatattttg attactgggg ccaaggagtc atggtcacag tctcctcagc tgaaacaaca      420
gccccatctg tctatccact ggctcctgga actgctctca aaagtaactc catggtgacc      480
```

```
ctgggatgcc tggtcaaggg ctatttccct gagccagtca ccgtgacctg gaactctgga    540
gccctgtcca gcggtgtgca caccttccca gctgtcctgc agtctggact ctacactctc    600
accagctcag tgactgtacc ctccagcacc tggtccagcc aggccgtcac ctgcaacgta    660
gcccacccgg ccagcagcac caaggtggac aagaaaattg tgccaaggga atgcaatcct    720
tgtggatgta caggctcaga agtatcatct gtcttcatct ccccccaaa gaccaaagat     780 gtgctcacca tcactctgac tcctaaggtc acgtgtgttg tggtagacat tagccagaat    840
gatcccgagg tccggttcag ctggtttata gatgacgtgg aagtccacac agctcagact    900
catgccccgg agaagcagtc caacagcact ttacgctcag tcagtgaact ccccatcgtg    960
caccgggact ggctcaatgg caagacgttc aaatgcaaag tcaacagtgg agcattccct    1020
gcccccatcg agaaaagcat ctccaaaccc gaaggcacac cacgaggtcc acaggtatac    1080
accatggcgc tcccaaggac agagatgacc cagagtcaag tcagtatcac ctgcatggta    1140
aaaggcttct atccccccaga catttatacg gagtggaaga tgaacgggca gccacaggaa    1200
aactacaaga cactccacc tacgatggac acagatggga gttacttcct ctacagcaag    1260
ctcaatgtaa agaaagaaac atggcagcag ggaaacactt tcacgtgttc tgtgctgcat    1320
gagggcctgc acaaccacca tactgagaag agtctctccc actctcctgg taaatga      1377
```

<210> SEQ ID NO 5
<211> LENGTH: 702
<212> TYPE: DNA
<213> ORGANISM: Rattus norvegicus
<220> FEATURE:
<223> OTHER INFORMATION: DNA coding for light chain of NZ-1 antibody

<400> SEQUENCE: 5

```
atgacatgga ctctactatt ccttgccttc cttcatcact taacagggtc atgtgcccag     60
tttgtgctta ctcagccaaa ctctgtgtct acgaatctcg gaagcacagt caaactgtct    120
tgtaagcgca gcactggtaa cattggaagc aattatgtga actggtacca gcagcatgag    180
ggaagatctc ccaccactat gatttatagg gatgataaga gaccagatgg agttcctgac    240
aggttctctg gctccattga cagatcttcc aactcagccc tcctgacaat caataatgtg    300
cagactgaag atgaagctga ctacttctgt cactcttaca gtagtggtat tgttttcggt    360
ggtggaacca agctcactgt cctaggtcag cccaagtcca ctcccacact cacagtattt    420
ccaccttcaa ctgaggagct ccagggaaac aaagccacac tggtgtgtct gatttctgat    480
ttctacccga gtgatgtgga agtggcctgg aaggcaaatg gtgcacctat ctcccagggt    540
gtggacactg caaatcccac caaacagggc aacaaataca tcgccagcag cttcttacgt    600
ttgacagcag aacagtggag atctcgcaac agttttacct gccaagttac acatgaaggg    660
aacactgtgg agaagagtct gtctcctgca gaatgtgtct ag                        702
```

<210> SEQ ID NO 6
<211> LENGTH: 8
<212> TYPE: PRT
<213> ORGANISM: Rattus norvegicus
<220> FEATURE:
<223> OTHER INFORMATION: heavy chain CDR1 of NZ-1 antibody

<400> SEQUENCE: 6

Gly Phe Thr Phe Ser Asn Tyr Gly
1               5

<210> SEQ ID NO 7
<211> LENGTH: 8

```
<212> TYPE: PRT
<213> ORGANISM: Rattus norvegicus
<220> FEATURE:
<223> OTHER INFORMATION: heavy chain CDR2 of NZ-1 antibody

<400> SEQUENCE: 7

Ile Ser Ala Gly Gly Asp Lys Thr
1               5

<210> SEQ ID NO 8
<211> LENGTH: 5
<212> TYPE: PRT
<213> ORGANISM: Rattus norvegicus
<220> FEATURE:
<223> OTHER INFORMATION: heavy chain CDR3 of NZ-1 antibody

<400> SEQUENCE: 8

Ala Lys Thr Ser Arg
1               5

<210> SEQ ID NO 9
<211> LENGTH: 8
<212> TYPE: PRT
<213> ORGANISM: Rattus norvegicus
<220> FEATURE:
<223> OTHER INFORMATION: light chain CDR1 of NZ-1 antibody

<400> SEQUENCE: 9

Thr Gly Asn Ile Gly Ser Asn Tyr
1               5

<210> SEQ ID NO 10
<211> LENGTH: 3
<212> TYPE: PRT
<213> ORGANISM: Rattus norvegicus
<220> FEATURE:
<223> OTHER INFORMATION: light chain CDR2 of NZ-1 antibody

<400> SEQUENCE: 10

Arg Asp Asp
1

<210> SEQ ID NO 11
<211> LENGTH: 8
<212> TYPE: PRT
<213> ORGANISM: Rattus norvegicus
<220> FEATURE:
<223> OTHER INFORMATION: light chain CDR3 of NZ-1 antibody

<400> SEQUENCE: 11

His Ser Tyr Ser Ser Gly Ile Val
1               5

<210> SEQ ID NO 12
<211> LENGTH: 24
<212> TYPE: DNA
<213> ORGANISM: Rattus norvegicus
<220> FEATURE:
<223> OTHER INFORMATION: DNA coding for heavy chain CDR1 of NZ-1
      antibody

<400> SEQUENCE: 12
ggattcactt tcagtaacta tggc                                           24

<210> SEQ ID NO 13
<211> LENGTH: 24
<212> TYPE: DNA
<213> ORGANISM: Rattus norvegicus
```

-continued

```
<220> FEATURE:
<223> OTHER INFORMATION: DNA coding for heavy chain CDR2 of NZ-1
      antibody

<400> SEQUENCE: 13
attagtgctg gtggtgataa aact                                             24

<210> SEQ ID NO 14
<211> LENGTH: 15
<212> TYPE: DNA
<213> ORGANISM: Rattus norvegicus
<220> FEATURE:
<223> OTHER INFORMATION: DNA coding for heavy chain CDR3 of NZ-1
      antibody

<400> SEQUENCE: 14
gcaaaaactt cccgg                                                       15

<210> SEQ ID NO 15
<211> LENGTH: 24
<212> TYPE: DNA
<213> ORGANISM: Rattus norvegicus
<220> FEATURE:
<223> OTHER INFORMATION: DNA coding for light chain CDR1 of NZ-1
      antibody

<400> SEQUENCE: 15
actggtaaca ttggaagcaa ttat                                             24

<210> SEQ ID NO 16
<211> LENGTH: 9
<212> TYPE: DNA
<213> ORGANISM: Rattus norvegicus
<220> FEATURE:
<223> OTHER INFORMATION: DNA coding for light chain CDR2 of NZ-1
      antibody

<400> SEQUENCE: 16 agggatgat                                                               9

<210> SEQ ID NO 17
<211> LENGTH: 24
<212> TYPE: DNA
<213> ORGANISM: Rattus norvegicus
<220> FEATURE:
<223> OTHER INFORMATION: DNA coding for light chain CDR3 of NZ-1
      antibody

<400> SEQUENCE: 17
cactcttaca gtagtggtat tgtt                                             24

<210> SEQ ID NO 18
<211> LENGTH: 117
<212> TYPE: PRT
<213> ORGANISM: Rattus norvegicus
<220> FEATURE:
<223> OTHER INFORMATION: VH domain of NZ-1 antibody

<400> SEQUENCE: 18

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Gly Met Ala Trp Val Arg Gln Thr Pro Thr Lys Gly Leu Glu Trp Ile
        35                  40                  45

Ala Ser Ile Ser Ala Gly Gly Asp Lys Thr Tyr Tyr Gly Asp Ser Val
```

```
                    50                  55                  60
Lys Gly Arg Phe Ser Ile Ser Arg Asp Asn Ala Lys Thr Thr His Tyr
 65                  70                  75                  80

Leu Gln Met Asp Ser Leu Arg Ser Glu Asp Thr Ala Thr Tyr Tyr Cys
                     85                  90                  95

Ala Lys Thr Ser Arg Val Tyr Phe Asp Tyr Trp Gly Gln Gly Val Met
                    100                 105                 110

Val Thr Val Ser Ser
                115

<210> SEQ ID NO 19
<211> LENGTH: 114
<212> TYPE: PRT
<213> ORGANISM: Rattus norvegicus
<220> FEATURE:
<223> OTHER INFORMATION: VL domain of NZ-1 antibody

<400> SEQUENCE: 19

Ala Gln Phe Val Leu Thr Gln Pro Asn Ser Val Ser Thr Asn Leu Gly
  1               5                  10                  15

Ser Thr Val Lys Leu Ser Cys Lys Arg Ser Thr Gly Asn Ile Gly Ser
                 20                  25                  30

Asn Tyr Val Asn Trp Tyr Gln Gln His Glu Gly Arg Ser Pro Thr Thr
             35                  40                  45

Met Ile Tyr Arg Asp Asp Lys Arg Pro Asp Gly Val Pro Asp Arg Phe
         50                  55                  60

Ser Gly Ser Ile Asp Arg Ser Ser Asn Ser Ala Leu Leu Thr Ile Asn
 65                  70                  75                  80

Asn Val Gln Thr Glu Asp Glu Ala Asp Tyr Phe Cys His Ser Tyr Ser
                 85                  90                  95

Ser Gly Ile Val Phe Gly Gly Gly Thr Lys Leu Thr Val Leu Gly Gln
                100                 105                 110

Pro Lys

<210> SEQ ID NO 20
<211> LENGTH: 100
<212> TYPE: PRT
<213> ORGANISM: Rattus norvegicus
<220> FEATURE:
<223> OTHER INFORMATION: CH1 domain of NZ-1 antibody

<400> SEQUENCE: 20

Ala Glu Thr Thr Ala Pro Ser Val Tyr Pro Leu Ala Pro Gly Thr Ala
  1               5                  10                  15

Leu Lys Ser Asn Ser Met Val Thr Leu Gly Cys Leu Val Lys Gly Tyr
                 20                  25                  30

Phe Pro Glu Pro Val Thr Val Thr Trp Asn Ser Gly Ala Leu Ser Ser
             35                  40                  45

Gly Val His Thr Phe Pro Ala Val Leu Gln Ser Gly Leu Tyr Thr Leu
         50                  55                  60

Thr Ser Ser Val Thr Val Pro Ser Ser Thr Trp Ser Ser Gln Ala Val
 65                  70                  75                  80

Thr Cys Asn Val Ala His Pro Ala Ser Ser Thr Lys Val Asp Lys Lys
                 85                  90                  95

Ile Val Pro Arg
            100

<210> SEQ ID NO 21
```

```
<211> LENGTH: 101
<212> TYPE: PRT
<213> ORGANISM: Rattus norvegicus
<220> FEATURE:
<223> OTHER INFORMATION: CL domain of NZ-1 antibody

<400> SEQUENCE: 21

Ser Thr Pro Thr Leu Thr Val Phe Pro Pro Ser Thr Glu Glu Leu Gln
1               5                   10                  15

Gly Asn Lys Ala Thr Leu Val Cys Leu Ile Ser Asp Phe Tyr Pro Ser
            20                  25                  30

Asp Val Glu Val Ala Trp Lys Ala Asn Gly Ala Pro Ile Ser Gln Gly
        35                  40                  45

Val Asp Thr Ala Asn Pro Thr Lys Gln Gly Asn Lys Tyr Ile Ala Ser
    50                  55                  60

Ser Phe Leu Arg Leu Thr Ala Glu Gln Trp Arg Ser Arg Asn Ser Phe
65                  70                  75                  80

Thr Cys Gln Val Thr His Glu Gly Asn Thr Val Glu Lys Ser Leu Ser
                85                  90                  95

Pro Ala Glu Cys Val
            100

<210> SEQ ID NO 22
<211> LENGTH: 227
<212> TYPE: PRT
<213> ORGANISM: Mus musculus
<220> FEATURE:
<223> OTHER INFORMATION: Fc domain of antibody

<400> SEQUENCE: 22

Pro Pro Leu Lys Glu Cys Pro Pro Cys Ala Ala Pro Asp Leu Leu Gly
1               5                   10                  15

Gly Pro Ser Val Phe Ile Phe Pro Pro Lys Ile Lys Asp Val Leu Met
            20                  25                  30

Ile Ser Leu Ser Pro Met Val Thr Cys Val Val Val Asp Val Ser Glu
        35                  40                  45

Asp Asp Pro Asp Val Gln Ile Ser Trp Phe Val Asn Asn Val Glu Val
    50                  55                  60

His Thr Ala Gln Thr Gln Thr His Arg Glu Asp Tyr Asn Ser Thr Leu
65                  70                  75                  80

Arg Val Val Ser Ala Leu Pro Ile Gln His Gln Asp Trp Met Ser Gly
                85                  90                  95

Lys Glu Phe Lys Cys Lys Val Asn Asn Arg Ala Leu Pro Ser Pro Ile
            100                 105                 110

Glu Lys Thr Ile Ser Lys Pro Arg Gly Pro Val Arg Ala Pro Gln Val
        115                 120                 125

Tyr Val Leu Pro Pro Pro Ala Glu Glu Met Thr Lys Lys Glu Phe Ser
    130                 135                 140

Leu Thr Cys Met Ile Thr Gly Phe Leu Pro Ala Glu Ile Ala Val Asp
145                 150                 155                 160

Trp Thr Ser Asn Gly Arg Thr Glu Gln Asn Tyr Lys Asn Thr Ala Thr
                165                 170                 175

Val Leu Asp Ser Asp Gly Ser Tyr Phe Met Tyr Ser Lys Leu Arg Val
            180                 185                 190

Gln Lys Ser Thr Trp Glu Arg Gly Ser Leu Phe Ala Cys Ser Val Val
        195                 200                 205

His Glu Gly Leu His Asn His Leu Thr Thr Lys Thr Ile Ser Arg Ser
    210                 215                 220
```

Leu Gly Lys
225

<210> SEQ ID NO 23
<211> LENGTH: 465
<212> TYPE: PRT
<213> ORGANISM: artificial
<220> FEATURE:
<223> OTHER INFORMATION: heavy chain of mouse-rat chimeric NZ-1 antibody

<400> SEQUENCE: 23

Met Asp Phe Arg Leu Ser Leu Ala Phe Leu Val Leu Ile Lys Gly
1               5                   10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Gly Met Ala Trp Val Arg Gln Thr Pro Thr Lys Gly Leu
    50                  55                  60

Glu Trp Ile Ala Ser Ile Ser Ala Gly Gly Asp Lys Thr Tyr Tyr Gly
65                  70                  75                  80

Asp Ser Val Lys Gly Arg Phe Ser Ile Ser Arg Asp Asn Ala Lys Thr
                85                  90                  95

Thr His Tyr Leu Gln Met Asp Ser Leu Arg Ser Glu Asp Thr Ala Thr
            100                 105                 110

Tyr Tyr Cys Ala Lys Thr Ser Arg Val Tyr Phe Asp Tyr Trp Gly Gln
        115                 120                 125

Gly Val Met Val Thr Val Ser Ser Ala Glu Thr Thr Ala Pro Ser Val
    130                 135                 140

Tyr Pro Leu Ala Pro Gly Thr Ala Leu Lys Ser Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ala Leu Ser Ser Gly Val His Thr Phe Pro Ala Val
            180                 185                 190

Leu Gln Ser Gly Leu Tyr Thr Leu Thr Ser Ser Val Thr Val Pro Ser
        195                 200                 205

Ser Thr Trp Ser Ser Gln Ala Val Thr Cys Asn Val Ala His Pro Ala
    210                 215                 220

Ser Ser Thr Lys Val Asp Lys Lys Ile Val Pro Arg Arg Ser Pro Pro
225                 230                 235                 240

Leu Lys Glu Cys Pro Pro Cys Ala Ala Pro Asp Leu Leu Gly Gly Pro
                245                 250                 255

Ser Val Phe Ile Phe Pro Pro Lys Ile Lys Asp Val Leu Met Ile Ser
            260                 265                 270

Leu Ser Pro Met Val Thr Cys Val Val Asp Val Ser Glu Asp Asp
        275                 280                 285

Pro Asp Val Gln Ile Ser Trp Phe Val Asn Asn Val Glu Val His Thr
    290                 295                 300

Ala Gln Thr Gln Thr His Arg Glu Asp Tyr Asn Ser Thr Leu Arg Val
305                 310                 315                 320

Val Ser Ala Leu Pro Ile Gln His Gln Asp Trp Met Ser Gly Lys Glu
                325                 330                 335

Phe Lys Cys Lys Val Asn Asn Arg Ala Leu Pro Ser Pro Ile Glu Lys
            340                 345                 350

```
Thr Ile Ser Lys Pro Arg Gly Pro Val Arg Ala Pro Gln Val Tyr Val
            355                 360                 365

Leu Pro Pro Ala Glu Glu Met Thr Lys Lys Glu Phe Ser Leu Thr
        370                 375                 380

Cys Met Ile Thr Gly Phe Leu Pro Ala Glu Ile Ala Val Asp Trp Thr
385                 390                 395                 400

Ser Asn Gly Arg Thr Glu Gln Asn Tyr Lys Asn Thr Ala Thr Val Leu
                405                 410                 415

Asp Ser Asp Gly Ser Tyr Phe Met Tyr Ser Lys Leu Arg Val Gln Lys
            420                 425                 430

Ser Thr Trp Glu Arg Gly Ser Leu Phe Ala Cys Ser Val Val His Glu
        435                 440                 445

Gly Leu His Asn His Leu Thr Thr Lys Thr Ile Ser Arg Ser Leu Gly
    450                 455                 460

Lys
465

<210> SEQ ID NO 24
<211> LENGTH: 1398
<212> TYPE: DNA
<213> ORGANISM: artificial
<220> FEATURE:
<223> OTHER INFORMATION: DNA coding for heavy chain of mouse-rat
      chimeric NZ-1 antibody

<400> SEQUENCE: 24
atggacttca ggctcagctt ggctttcctt gtccttttaa taaaaggtgt ccagtgtgag      60
gtgcagctgg tggagtctgg gggaggctta gtgcagcctg aaggtccct gaaactctcc    120 tgtgcagcct caggattcac tttcagtaac atgggcatgg cctgggtccg ccagactcca    180
acgaagggtc tggagtggat cgcatccatt agtgctggtg gtgataaaac ttactatgga    240
gactccgtga agggccgatt cagtatctcc agagataatg caaaaaccac ccactacttg    300
caaatggaca gtctgaggtc tgaggacacg gccacttatt actgtgcaaa aacttcccgg    360 gtatatttg attactgggg ccaaggagtc atggtcacag tctcctcagc tgaaacaaca    420
gccccatctg tctatccact ggctcctgga actgctctca aaagtaactc catggtgacc    480
ctgggatgcc tggtcaaggg ctatttccct gagccagtca ccgtgacctg aactctgga    540 gccctgtcca gcggtgtgca caccttccca gctgtcctgc agtctggact ctacactctc    600
accagctcag tgactgtacc ctccagcacc tggtccagcc aggccgtcac ctgcaacgta    660
gcccacccgg ccagcagcac caaggtggac aagaaaattg tgccaaggag atctcctcca    720
ctcaaagagt gtccccatg cgcagctcca gacctcttgg gtggaccatc cgtcttcatc    780
ttccctccaa agatcaagga tgtactcatg atctcccga gccccatggt cacatgtgtg    840
gtggtggatg tgagcgagga tgacccagac gtccagatca gctggttgt gaacaacgtg    900 gaagtacaca cagctcagac acaaacccat agagaggatt acaacagtac tctccgggtg    960
gtcagtgccc tccccatcca gcaccaggac tggatgagtg gcaaggagtt caatgcaag   1020 gtcaacaaca gagccctcc atccccatc gagaaaacca tctcaaaacc agagggcca    1080 gtaagagctc cacaggtata tgtcttgcct ccaccagcag aagagatgac taagaaagag   1140
ttcagtctga cctgcatgat cacaggcttc ttacctgccg aaattgctgt ggactggacc   1200
agcaatgggc gtacagagca aaactacaag aacaccgcaa cagtcctgga ctctgatggt   1260
tcttacttca tgtacagcaa gctcagagta caaagagca cttgggaaag aggaagtctt   1320
ttcgcctgct cagtggtcca cgagggtctg cacaatcacc ttacgactaa gaccatctcc   1380
```

```
cggtctctgg gtaaatga                                                      1398
```

<210> SEQ ID NO 25
<211> LENGTH: 20
<212> TYPE: DNA
<213> ORGANISM: artificial
<220> FEATURE:
<223> OTHER INFORMATION: forward primer for amplification of heavy chain
      of NZ-1 antibody

<400> SEQUENCE: 25

```
tcctcaccat ggacttcagg                                                      20
```

<210> SEQ ID NO 26
<211> LENGTH: 20
<212> TYPE: DNA
<213> ORGANISM: artificial
<220> FEATURE:
<223> OTHER INFORMATION: reverse primer for amplification of heavy chain
      of NZ-1 antibody

<400> SEQUENCE: 26

```
tcatttacca ggagagtggg                                                      20
```

<210> SEQ ID NO 27
<211> LENGTH: 29
<212> TYPE: DNA
<213> ORGANISM: artificial
<220> FEATURE:
<223> OTHER INFORMATION: forward primer for amplification of light chain
      of NZ-1 antibody

<400> SEQUENCE: 27

```
ccaggatcca ccatgacatg gactctact                                            29
```

<210> SEQ ID NO 28
<211> LENGTH: 29
<212> TYPE: DNA
<213> ORGANISM: artificial
<220> FEATURE:
<223> OTHER INFORMATION: reverse primer for amplification of light chain
      of NZ-1 antibody

<400> SEQUENCE: 28

```
ggtgaattcc tagacacatt ctgcaggag                                            29
```

<210> SEQ ID NO 29
<211> LENGTH: 24
<212> TYPE: DNA
<213> ORGANISM: artificial
<220> FEATURE:
<223> OTHER INFORMATION: forward primer for amplification of VH and CH1
      domain of NZ-1 antibody

<400> SEQUENCE: 29

```
ccagaattct cctcaccatg gact                                                 24
```

<210> SEQ ID NO 30
<211> LENGTH: 29
<212> TYPE: DNA
<213> ORGANISM: artificial
<220> FEATURE:
<223> OTHER INFORMATION: reverse primer for amplification of VH and CH1
      domain of NZ-1 antibody

<400> SEQUENCE: 30

```
tggagatctc cttggcacaa ttttcttgt                                            29
```

<210> SEQ ID NO 31
<211> LENGTH: 20
<212> TYPE: DNA
<213> ORGANISM: Artificial
<220> FEATURE:
<223> OTHER INFORMATION: forward primer for amplification of VH domain of NZ-1 antibody

<400> SEQUENCE: 31
tcctcaccat ggacttcagg                                          20

<210> SEQ ID NO 32
<211> LENGTH: 20
<212> TYPE: DNA
<213> ORGANISM: Artificial
<220> FEATURE:
<223> OTHER INFORMATION: reverse primer for amplification of VH domain of NZ-1 antibody

<400> SEQUENCE: 32
ttcagctgag gagactgtga                                          20

<210> SEQ ID NO 33
<211> LENGTH: 20
<212> TYPE: DNA
<213> ORGANISM: Artificial
<220> FEATURE:
<223> OTHER INFORMATION: forward primer for amplification of VL domain of NZ-1 antibody

<400> SEQUENCE: 33
accatgacat ggactctact                                          20

<210> SEQ ID NO 34
<211> LENGTH: 19
<212> TYPE: DNA
<213> ORGANISM: Artificial
<220> FEATURE:
<223> OTHER INFORMATION: reverse primer for amplification of VL domain of NZ-1 antibody

<400> SEQUENCE: 34
cttgggctga cctaggaca                                           19

<210> SEQ ID NO 35
<211> LENGTH: 328
<212> TYPE: PRT
<213> ORGANISM: Homo Sapiens
<220> FEATURE:
<221> NAME/KEY: MISC_FEATURE
<223> OTHER INFORMATION: CH1, CH2, CH3 and hinge domain of human IgG1

<400> SEQUENCE: 35

Thr Lys Gly Pro Ser Val Phe Pro Leu Ala Pro Cys Ser Arg Ser Thr
 1               5                  10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Asn Phe Gly Thr Gln Thr Tyr Thr
65                  70                  75                  80

Cys Asn Val Asp His Lys Pro Ser Asn Thr Lys Val Asp Lys Thr Val

```
                        85                  90                  95
Glu Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
            115                 120                 125

Lys Asp Thr Leu Met Ile Ser Arg Thr Pro Glu Val Thr Cys Val Val
            130                 135                 140

Val Asp Val Ser His Glu Asp Pro Glu Val Gln Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
            195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
            275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 36
<211> LENGTH: 109
<212> TYPE: PRT
<213> ORGANISM: Homo Sapiens
<220> FEATURE:
<221> NAME/KEY: MISC_FEATURE
<223> OTHER INFORMATION: CL domain of human IgG1

<400> SEQUENCE: 36

Gly Ile Arg Thr Val Ala Ala Pro Ser Val Phe Ile Phe Pro Pro Ser
1               5                   10                  15

Asp Glu Gln Leu Lys Ser Gly Thr Ala Ser Val Val Cys Leu Leu Asn
            20                  25                  30

Asn Phe Tyr Pro Arg Glu Ala Lys Val Gln Trp Lys Val Asp Asn Ala
        35                  40                  45

Leu Gln Ser Gly Asn Ser Gln Glu Ser Val Thr Glu Gln Asp Ser Lys
    50                  55                  60

Asp Ser Thr Tyr Ser Leu Ser Ser Thr Leu Thr Leu Ser Lys Ala Asp
65                  70                  75                  80

Tyr Glu Lys His Lys Val Tyr Ala Cys Glu Val Thr His Gln Gly Leu
                85                  90                  95

Ser Ser Pro Val Thr Lys Ser Phe Asn Arg Gly Glu Cys
            100                 105
```

```
<210> SEQ ID NO 37
<211> LENGTH: 468
<212> TYPE: PRT
<213> ORGANISM: Artificial
<220> FEATURE:
<223> OTHER INFORMATION: Heavy chain of human-rat chimeric NZ-1 antibody

<400> SEQUENCE: 37
```

| | | | | | | | | | | | | | | |
|---|---|---|---|---|---|---|---|---|---|---|---|---|---|---|
| Met | Asp | Phe | Arg | Leu | Ser | Leu | Ala | Phe | Leu | Val | Leu | Ile | Lys | Gly |
| 1 | | | | 5 | | | | | 10 | | | | | 15 |

| Val | Gln | Cys | Glu | Val | Gln | Leu | Val | Glu | Ser | Gly | Gly | Leu | Val | Gln |
|---|---|---|---|---|---|---|---|---|---|---|---|---|---|---|
| | | | 20 | | | | | 25 | | | | | 30 | |

| Pro | Gly | Arg | Ser | Leu | Lys | Leu | Ser | Cys | Ala | Ala | Ser | Gly | Phe | Thr | Phe |
|---|---|---|---|---|---|---|---|---|---|---|---|---|---|---|---|
| | | 35 | | | | | 40 | | | | | 45 | | | |

| Ser | Asn | Tyr | Gly | Met | Ala | Trp | Val | Arg | Gln | Thr | Pro | Thr | Lys | Gly | Leu |
|---|---|---|---|---|---|---|---|---|---|---|---|---|---|---|---|
| | 50 | | | | | 55 | | | | | 60 | | | | |

| Glu | Trp | Ile | Ala | Ser | Ile | Ser | Ala | Gly | Gly | Asp | Lys | Thr | Tyr | Tyr | Gly |
|---|---|---|---|---|---|---|---|---|---|---|---|---|---|---|---|
| 65 | | | | | 70 | | | | | 75 | | | | | 80 |

| Asp | Ser | Val | Lys | Gly | Arg | Phe | Ser | Ile | Ser | Arg | Asp | Asn | Ala | Lys | Thr |
|---|---|---|---|---|---|---|---|---|---|---|---|---|---|---|---|
| | | | | 85 | | | | | 90 | | | | | 95 | |

| Thr | His | Tyr | Leu | Gln | Met | Asp | Ser | Leu | Arg | Ser | Glu | Asp | Thr | Ala | Thr |
|---|---|---|---|---|---|---|---|---|---|---|---|---|---|---|---|
| | | | | 100 | | | | | 105 | | | | | 110 | |

| Tyr | Tyr | Cys | Ala | Lys | Thr | Ser | Arg | Val | Tyr | Phe | Asp | Tyr | Trp | Gly | Gln |
|---|---|---|---|---|---|---|---|---|---|---|---|---|---|---|---|
| | | 115 | | | | | 120 | | | | | 125 | | | |

| Gly | Val | Met | Val | Thr | Val | Ser | Ser | Ala | Glu | Gly | Ser | Thr | Lys | Gly | Pro |
|---|---|---|---|---|---|---|---|---|---|---|---|---|---|---|---|
| | 130 | | | | | 135 | | | | | 140 | | | | |

| Ser | Val | Phe | Pro | Leu | Ala | Pro | Cys | Ser | Arg | Ser | Thr | Ser | Glu | Ser | Thr |
|---|---|---|---|---|---|---|---|---|---|---|---|---|---|---|---|
| 145 | | | | | 150 | | | | | 155 | | | | | 160 |

| Ala | Ala | Leu | Gly | Cys | Leu | Val | Lys | Asp | Tyr | Phe | Pro | Glu | Pro | Val | Thr |
|---|---|---|---|---|---|---|---|---|---|---|---|---|---|---|---|
| | | | | 165 | | | | | 170 | | | | | 175 | |

| Val | Ser | Trp | Asn | Ser | Gly | Ala | Leu | Thr | Ser | Gly | Val | His | Thr | Phe | Pro |
|---|---|---|---|---|---|---|---|---|---|---|---|---|---|---|---|
| | | | | 180 | | | | | 185 | | | | | 190 | |

| Ala | Val | Leu | Gln | Ser | Ser | Gly | Leu | Tyr | Ser | Leu | Ser | Ser | Val | Val | Thr |
|---|---|---|---|---|---|---|---|---|---|---|---|---|---|---|---|
| | | 195 | | | | | 200 | | | | | 205 | | | |

| Val | Pro | Ser | Ser | Asn | Phe | Gly | Thr | Gln | Thr | Tyr | Thr | Cys | Asn | Val | Asp |
|---|---|---|---|---|---|---|---|---|---|---|---|---|---|---|---|
| | 210 | | | | | 215 | | | | | 220 | | | | |

| His | Lys | Pro | Ser | Asn | Thr | Lys | Val | Asp | Lys | Thr | Val | Glu | Pro | Lys | Ser |
|---|---|---|---|---|---|---|---|---|---|---|---|---|---|---|---|
| 225 | | | | | 230 | | | | | 235 | | | | | 240 |

| Cys | Asp | Lys | Thr | His | Thr | Cys | Pro | Pro | Cys | Pro | Ala | Pro | Glu | Leu | Leu |
|---|---|---|---|---|---|---|---|---|---|---|---|---|---|---|---|
| | | | | 245 | | | | | 250 | | | | | 255 | |

| Gly | Gly | Pro | Ser | Val | Phe | Leu | Phe | Pro | Pro | Lys | Pro | Lys | Asp | Thr | Leu |
|---|---|---|---|---|---|---|---|---|---|---|---|---|---|---|---|
| | | | | 260 | | | | | 265 | | | | | 270 | |

| Met | Ile | Ser | Arg | Thr | Pro | Glu | Val | Thr | Cys | Val | Val | Val | Asp | Val | Ser |
|---|---|---|---|---|---|---|---|---|---|---|---|---|---|---|---|
| | | 275 | | | | | 280 | | | | | 285 | | | |

| His | Glu | Asp | Pro | Glu | Val | Gln | Phe | Asn | Trp | Tyr | Val | Asp | Gly | Val | Glu |
|---|---|---|---|---|---|---|---|---|---|---|---|---|---|---|---|
| | 290 | | | | | 295 | | | | | 300 | | | | |

| Val | His | Asn | Ala | Lys | Thr | Lys | Pro | Arg | Glu | Glu | Gln | Tyr | Asn | Ser | Thr |
|---|---|---|---|---|---|---|---|---|---|---|---|---|---|---|---|
| 305 | | | | | 310 | | | | | 315 | | | | | 320 |

| Tyr | Arg | Val | Val | Ser | Val | Leu | Thr | Val | Leu | His | Gln | Asp | Trp | Leu | Asn |
|---|---|---|---|---|---|---|---|---|---|---|---|---|---|---|---|
| | | | | 325 | | | | | 330 | | | | | 335 | |

| Gly | Lys | Glu | Tyr | Lys | Cys | Lys | Val | Ser | Asn | Lys | Ala | Leu | Pro | Ala | Pro |
|---|---|---|---|---|---|---|---|---|---|---|---|---|---|---|---|
| | | | | 340 | | | | | 345 | | | | | 350 | |

| Ile | Glu | Lys | Thr | Ile | Ser | Lys | Ala | Lys | Gly | Gln | Pro | Arg | Glu | Pro | Gln |
|---|---|---|---|---|---|---|---|---|---|---|---|---|---|---|---|
| | | 355 | | | | | 360 | | | | | 365 | | | |

| Val | Tyr | Thr | Leu | Pro | Pro | Ser | Arg | Asp | Glu | Leu | Thr | Lys | Asn | Gln | Val |
|---|---|---|---|---|---|---|---|---|---|---|---|---|---|---|---|
| | 370 | | | | | 375 | | | | | 380 | | | | |

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 38
<211> LENGTH: 1407
<212> TYPE: DNA
<213> ORGANISM: Artificial
<220> FEATURE:
<223> OTHER INFORMATION: DNA coding for heavy chain of human-rat
      chimeric NZ-1 antibody

<400> SEQUENCE: 38
atggacttca ggctcagctt ggctttcctt gtccttttaa taaaaggtgt ccagtgtgag      60
gtgcagctgg tggagtctgg gggaggctta gtgcagcctg aaggtccct gaaactctcc     120 tgtgcagcct caggattcac tttcagtaac tatggcatgg cctgggtccg ccagactcca     180
acgaagggtc tggagtggat cgcatccatt agtgctggtg gtgataaaac ttactatgga     240
gactccgtga agggccgatt cagtatctcc agagataatg caaaaaccac ccactacttg     300
caaatggaca gtctgaggtc tgaggacacg gccacttatt actgtgcaaa aacttcccgg     360
gtatattttg attactgggg ccaaggagtc atggtcacag tctcctcagc tgaaggatcc     420
accaagggcc catcggtctt ccccctggcg ccctgctcca ggagcacctc cgagagcaca     480
gcggccctgg gctgcctggt caaggactac ttccccgaac cggtgacggt gtcgtggaac     540
tcaggcgctc tgaccagcgg cgtgcacacc ttcccagctg tcctacagtc ctcaggactc     600
tactccctca gcagcgtggt gaccgtgccc tccagcaact tcggcaccca gacctacacc     660
tgcaacgtag atcacaagcc cagcaacacc aaggtggaca gacagttga gcccaaatct     720 tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acgtgcgtgg tggtggacgt gagccacgaa ga ccccgagg tccagttcaa ctggtacgtg     900
gacggcgtgg aggtgcataa tgccaagaca agccgcgggg aggagcagta caacagcacg     960
taccgtgtgg tcagcgtcct caccgtcctg caccaggact ggctgaatgg caaggagtac    1020
aaatgcaagg tctccaacaa agccctccca gccccatcg agaaaaccat ctccaaagcc    1080
aaagggcagc ccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ttacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                        1407

<210> SEQ ID NO 39
```

<211> LENGTH: 241
<212> TYPE: PRT
<213> ORGANISM: Artificial
<220> FEATURE:
<223> OTHER INFORMATION: Light chain of human-rat chimeric NZ-1 antibody

<400> SEQUENCE: 39

```
Met Thr Trp Thr Leu Leu Phe Leu Ala Phe Leu His His Leu Thr Gly
1               5                   10                  15

Ser Cys Ala Gln Phe Val Leu Thr Gln Pro Asn Ser Val Ser Thr Asn
            20                  25                  30

Leu Gly Ser Thr Val Lys Leu Ser Cys Lys Arg Ser Thr Gly Asn Ile
        35                  40                  45

Gly Ser Asn Tyr Val Asn Trp Tyr Gln Gln His Glu Gly Arg Ser Pro
    50                  55                  60

Thr Thr Met Ile Tyr Arg Asp Asp Lys Arg Pro Asp Gly Val Pro Asp
65                  70                  75                  80

Arg Phe Ser Gly Ser Ile Asp Arg Ser Ser Asn Ser Ala Leu Leu Thr
                85                  90                  95

Ile Asn Asn Val Gln Thr Glu Asp Glu Ala Asp Tyr Phe Cys His Ser
            100                 105                 110

Tyr Ser Ser Gly Ile Val Phe Gly Gly Gly Thr Lys Leu Thr Val Leu
        115                 120                 125

Gly Gln Pro Lys Gly Ile Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 40
<211> LENGTH: 726
<212> TYPE: DNA
<213> ORGANISM: Artificial
<220> FEATURE:
<223> OTHER INFORMATION: DNA coding for light chain of human-rat
    chimeric NZ-1 antibody

<400> SEQUENCE: 40

| | | |
|---|---|---|
| atgacatgga ctctactatt ccttgccttc cttcatcact taacagggtc atgtgcccag | 60 |
| tttgtgctta ctcagccaaa ctctgtgtct acgaatctcg aagcacagt caaactgtct | 120 |
| tgtaagcgca gcactggtaa cattggaagc aattatgtga actggtacca gcagcatgag | 180 |
| ggaagatctc ccaccactat gatttatagg gatgataaga gaccagatgg agttcctgac | 240 |
| aggttctctg gctccattga cagatcttcc aactcagccc tcctgacaat caataatgtg | 300 |
| cagactgaag atgaagctga ctacttctgt cactcttaca gtagtggtat tgttttcggt | 360 |
| ggtggaacca agctcactgt cctaggtcag cccaagggaa ttcgaactgt ggctgcacca | 420 |

| | | | | | | |
|---|---|---|---|---|---|---|
| tctgtcttca | tcttcccgcc | atctgatgag | cagttgaaat | ctggaactgc | ctctgttgtg | 480 |
| tgcctgctga | ataacttcta | tcccagagag | gccaaagtac | agtggaaggt | ggataacgcc | 540 |
| ctccaatcgg | gtaactccca | ggagagtgtc | acagagcagg | acagcaagga | cagcacctac | 600 |
| agcctcagca | gcaccctgac | gctgagcaaa | gcagactacg | agaaacacaa | agtctacgcc | 660 |
| tgcgaagtca | cccatcaggg | cctgagctcg | cccgtcacaa | agagcttcaa | caggggagag | 720 |
| tgttag | | | | | | 726 |